(12) United States Patent
Nguyen et al.

(10) Patent No.: US 11,952,611 B2
(45) Date of Patent: Apr. 9, 2024

(54) METHODS AND SYSTEMS FOR DETECTION OF ANTIBIOTIC RESISTANCE

(71) Applicant: Laboratory Corporation of America Holdings, Burlington, NC (US)

(72) Inventors: Minh Mindy Bao Nguyen, Shoreview, MN (US); Dwight L. Anderson, Minneapolis, MN (US); Jose S. Gil, Winnetka, CA (US); Stephen E. Erickson, White Bear Township, MN (US); Matthew J. Brown, Burlington, NC (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

(21) Appl. No.: 16/026,462

(22) Filed: Jul. 3, 2018

(65) Prior Publication Data
US 2019/0010534 A1    Jan. 10, 2019

Related U.S. Application Data

(60) Provisional application No. 62/529,689, filed on Jul. 7, 2017.

(51) Int. Cl.
| | | |
|---|---|---|
| *C12Q 1/14* | (2006.01) | |
| *C12Q 1/06* | (2006.01) | |
| *C12Q 1/10* | (2006.01) | |
| *C12Q 1/18* | (2006.01) | |
| *C12Q 1/66* | (2006.01) | |
| *G01N 33/569* | (2006.01) | |
| *C12N 15/73* | (2006.01) | |
| *C12Q 1/689* | (2018.01) | |

(52) U.S. Cl.
CPC ............ *C12Q 1/14* (2013.01); *C12Q 1/06* (2013.01); *C12Q 1/10* (2013.01); *C12Q 1/18* (2013.01); *C12Q 1/66* (2013.01); *G01N 33/56911* (2013.01); *C12N 15/73* (2013.01); *C12Q 1/689* (2013.01)

(58) Field of Classification Search
None
See application file for complete search history.

(56) References Cited

U.S. PATENT DOCUMENTS

| | | | |
|---|---|---|---|
| 10,519,483 B2 * | 12/2019 | Anderson | ............ G01N 33/569 |
| 2005/0003346 A1 * | 1/2005 | Voorhees | .................. C12Q 1/04 |
| | | | 435/5 |
| 2007/0178450 A1 * | 8/2007 | Wheeler | .................. C12Q 1/06 |
| | | | 435/5 |
| 2009/0047658 A1 | 2/2009 | Mulvey et al. | |
| 2009/0258341 A1 * | 10/2009 | Voorhees | ................. C12N 7/00 |
| | | | 435/5 |
| 2009/0286225 A1 | 11/2009 | Wheeler et al. | |
| 2015/0218616 A1 | 8/2015 | Anderson et al. | |
| 2017/0121688 A1 | 5/2017 | Gil et al. | |

FOREIGN PATENT DOCUMENTS

| | | |
|---|---|---|
| WO | 2008064241 | 5/2008 |
| WO | 2008124119 | 10/2008 |
| WO | 2018126266 | 7/2018 |

OTHER PUBLICATIONS

Bardarov et al., Diag. Microbiol. Infect. Dis., vol. 45, p. 53-61 (Year: 2004).*
Bardarov et al., "Detection And Drug-Susceptibility Testing of M. Tuberculosis From Sputum Samples Using Luciferase Reporter Phage: Comparison With the Mycobacteria Growth Indicator Tube (MGIT) System", Diagnostic Microbiology And Infectious Disease, vol. 45, Issue 1, Jan. 1, 2003, pp. 53-61.
PCT/US2018/040710 , "International Search Report and Written Opinion", dated Sep. 12, 2018, 12 pages.
CA 3,066,955, Office Action, dated Dec. 7, 2020, 4 pages.
PCT/US2018/040710, International Preliminary Report on Patentability, dated Jan. 16, 2020, 8 pages.
Application No. CA3,066,955 , Office Action, Mailed On Nov. 16, 2021, 3 pages.
Application No. CA3,066,955 , Office Action, Mailed On Nov. 4, 2022, 3 pages.
Application No. CN201880045428.4 , Office Action, Mailed On Feb. 24, 2023, 16 pages.
Application No. EP18750550.8 , Office Action, Mailed On Oct. 12, 2022, 6 pages.
Jacobs et al., "Rapid Assessment of Drug Susceptibilities of Mycobacterium Tuberculosis by Means of Luciferase Reporter Phages", Science, vol. 260, No. 5109, May 7, 1993, pp. 819-822.
Application No. JP2019-571605 , Office Action, Mailed On Sep. 12, 2022, 5 pages.
Application No. JP2019-571605 , Office Action, Mailed On Jan. 18, 2022, 7 pages.
Rees et al., "Simultaneous Identification and Susceptibility Determination to Multiple Antibiotics of Staphylococcus Aureus by Bacteriophage Amplification Detection Combined with Mass Spectrometry", Analytical Chemistry, vol. 87, No. 13, Jul. 7, 2015, pp. 6769-6777.

* cited by examiner

*Primary Examiner* — Shanon A. Foley
*Assistant Examiner* — Myron G Hill
(74) *Attorney, Agent, or Firm* — Kilpatrick Townsend & Stockton LLP

(57) ABSTRACT

Disclosed herein are methods and systems for rapid detection of antibiotic resistance of a microorganism in a sample. A modified recombinant phage is also disclosed which comprises an indicator gene in the late gene region. The specificity of infectious agents allows a specific microorganism to be targeted, and an indicator signal may be amplified to optimize assay sensitivity.

21 Claims, 1 Drawing Sheet

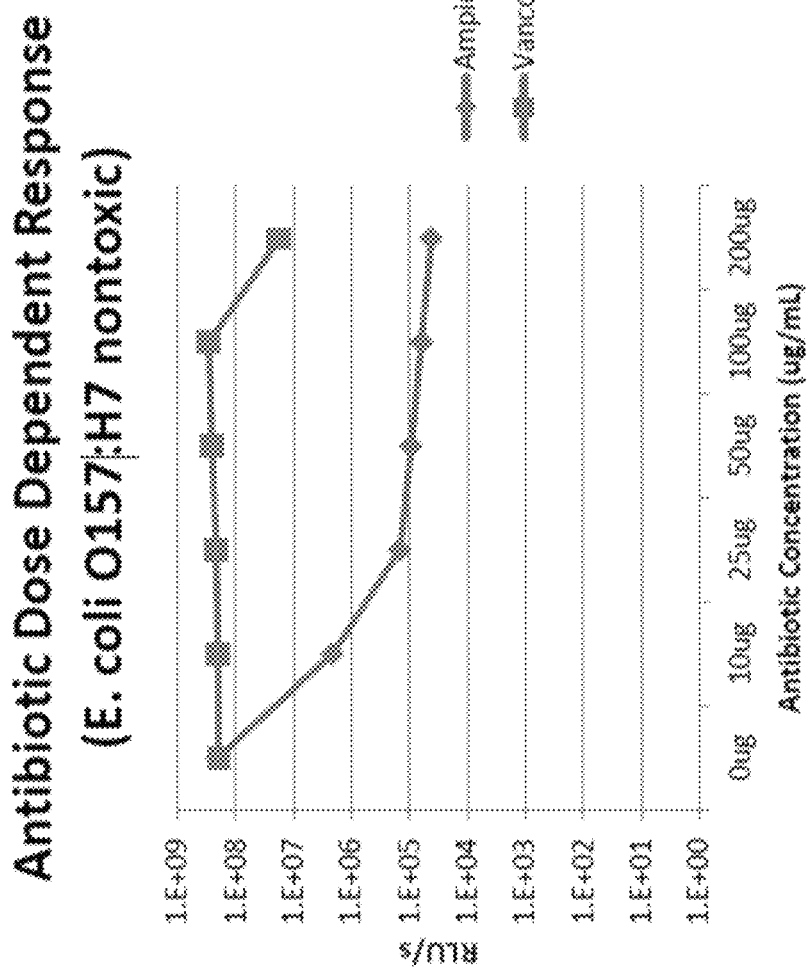

METHODS AND SYSTEMS FOR DETECTION OF ANTIBIOTIC RESISTANCE

CROSS-REFERENCE TO RELATED APPLICATIONS

This application claims the benefit and priority to U.S. Provisional Application Ser. No. 62/529,689, filed Jul. 7, 2017, the disclosures of this application are herein incorporated by reference in their entirety.

FIELD OF THE INVENTION

This invention relates to methods and systems for the detection of antibiotic resistance of microorganisms using infectious agents.

BACKGROUND

Antibiotics are widely used to treat infections caused by microorganisms. Some microorganisms are naturally resistant to a particular antibiotic, while others may acquire such resistance after being treated with the antibiotic for some time. Antibiotic resistance can cause undesired consequences; microorganisms still grow in the presence of the antibiotic, therefore exacerbating the infection, and the ineffective antibiotic may cause serious side effects, leading to circumstances, which can be life-threatening in some cases. Further, these antibiotic-resistant microorganisms may infect humans and animals, resulting in infections that are typically harder to treat than those caused by non-resistant bacteria. As a result, antibiotic resistance can lead to higher medical costs, prolonged hospital stays, and increased mortality.

Accordingly, detection of microorganisms that are resistant to particular antibiotics is of great importance. The ability of healthcare providers to determine whether microorganisms responsible for an infection present in the body are resistant to antibiotics is extremely important in selecting the correct treatment. Further, being able to determine the antibiotic resistance of microorganisms within a short timeframe from samples with low levels of microorganisms is vital to successful treatment of infections before they become severe.

Additionally, the ability to conduct colonization reference tests rapidly from samples with low levels of pathogens is beneficial in preventing the spread of antibiotic-resistant pathogens, particularly, nosocomial infections. For example, the use of rapid colonization reference tests (e.g., MRSA nasal swabs) capable of detecting low levels of pathogens can be used as a preventative measure to screen for patients colonizing antibiotic-resistant bacteria. Early and rapid detection of colonization by antibiotic-resistant bacteria allows for preventative measures to be put in place (e.g., methicillin-resistant *Staphylococcus aureus* (MRSA)). MRSA is a major cause of nosocomial infections and can cause severe and life-threatening infections. The total cost burden to the US health care system from MRSA infections is estimated to exceed $2.5 billion annually.

Current methods of antibiotic resistance detection, often require assays that are time-consuming, technically-demanding, and/or lack sufficient sensitivity. Typically, these assays involve immunoassays and molecular-based assays in cultured samples that require gel electrophoresis, real time PCR/multiplexing, and/or multi-locus sequence typing. These tests often require 24-48 hours to complete and/or lack sufficient sensitivity. Methods currently available typically require isolation and/or enrichment by culturing of microorganisms prior to detection, thus, requiring increased time-to-results. Therefore, there is a strong interest in a rapid and sensitive test to determine whether a microorganism of interest, e.g., a microorganism that caused an infection, is resistant to a particular antibiotic before using the antibiotic. The present invention excels as a rapid test for the detection of microorganism by not requiring isolation of the microorganisms prior to detection. This knowledge can aid clinicians in prescribing suitable antibiotics to timely control infections and increase the ability to prevent the spread of serious infections through active monitoring in healthcare settings.

SUMMARY

Embodiments of the invention comprise compositions and methods for the detection of antibiotic resistance of microorganisms. The invention may be embodied in a variety of ways.

In some embodiments, the disclosure provides methods of detecting antibiotic-resistant microorganisms in a sample comprising: (a) contacting the sample with an antibiotic, (b) contacting the sample with an infectious agent, wherein the infectious agent comprises an indicator gene and is specific to the microorganism, and wherein the indicator gene encodes an indicator protein product, and (c) detecting a signal produced by an indicator protein product, wherein detection of the signal is used to determine antibiotic resistance.

In some embodiments, the infectious agent is a recombinant phage and the microorganism is a bacterium. In further embodiments, the indicator gene encodes the indicator protein product that generates an intrinsic signal or an enzyme that generates signal upon reaction with substrate.

In some embodiments, the disclosure provides a method of determining effective dose of an antibiotic in killing a microorganism comprising: (a) incubating each of one or more of antibiotic solutions separately with one or more samples comprising the microorganism, wherein the concentrations of the one or more of antibiotic solutions are different and define a range, (b) incubating the microorganisms in the one or more of samples with an infectious agent comprising an indicator gene, and wherein the infectious agent is specific for the microorganism of interest, and (c) detecting an indicator protein product produced by the infectious agent in the one or more of samples, wherein detection of the indicator protein product in one or more of the plurality of samples indicates the concentrations of antibiotic solutions used to treat the one or more of the one or more of samples are not effective, and the lack of detection of the indicator protein indicates the antibiotic is effective, thereby determining the effective dose of the antibiotic.

In some embodiments, the disclosure provides a kit and a system for detecting antibiotic resistance comprising a recombinant phage having an indicator gene and an antibiotic.

Certain specific embodiments of the present invention make use of methods and construct described in US Patent Publication No. 2015/0218616, and incorporated by reference herein in its entirety.

BRIEF DESCRIPTION OF THE FIGURES

The present invention may be better understood by referring to the following non-limiting FIGURES.

FIG. 1 depicts one embodiment of the methods disclosed herein, showing a dose response of *E. coli* O157:H7 to ampicillin but not to vancomycin.

DETAILED DESCRIPTION OF THE INVENTION

Disclosed herein are compositions, methods and systems that demonstrate surprising speed and sensitivity for detecting antibiotic resistance of a microorganism. Detection can be achieved in a shorter timeframe than currently available methods. The detection uses genetically modified infectious agents in assays performed without isolation or culturing for enrichment, or in some embodiments with minimal incubation times during which microorganisms could potentially multiply. Some embodiments of the invention disclosed and described herein utilize the discovery that a single microorganism is capable of binding specific recognition agents, such as phages. Following infection by phage, phage replication may be detected via the production of an indicator moiety. The production of progeny phage, sometimes 100 progeny or greater per infecting parental phage, can result in a high level expression of an indicator moiety, and thus allows for greater detection ability of the microorganism. In this way, embodiments of the present invention can achieve tremendous signal amplification from as few as a single infected cell. Accordingly, antibiotic resistance can be detected by determining that pathogenic cells have survived a particular antibiotic treatment. For example, in some embodiments, the methods allow one to determine the number of cells that have survived a particular antibiotic treatment. In further embodiments, the methods allow one to determine a percentage of cells that have survived a particular antibiotic treatment.

The compositions, methods, systems and kits of the invention may comprise infectious agents for use in detection of antibiotic resistance of such microorganisms. In certain embodiments of the invention, a composition may comprise a recombinant phage having an indicator gene inserted into the phage genome and a composition comprising the antibiotic for which resistance is to be tested. In certain embodiments, expression of the indicator gene during phage replication following infection of a host bacterium results in production of a soluble indicator protein product. In certain embodiments, the indicator gene may be inserted into a late gene (i.e., class III) region of the phage. The phage may be derived from T7, T4, phage K (i.e., *Staphylococcus* phage K) or other natural phages. In certain embodiments, the antibiotic may be present in a plurality of solutions at different concentrations.

In some aspects, the invention comprises a method for detecting antibiotic resistance of a microorganism. In some embodiments, the disclosure provides methods for detecting antibiotic-resistant microorganisms in a sample comprising: (a) contacting the sample with an antibiotic, (b) contacting the sample with an infectious agent, wherein the infectious agent comprises an indicator gene and is specific to the microorganism, and wherein the indicator gene encodes an indicator protein product, and (c) detecting a signal produced by an indicator protein product, wherein detection of the signal is used to determine antibiotic resistance.

The methods may use an infectious agent for detection of the microorganism of interest. For example, in certain embodiments, the microorganism of interest is a bacterium and the infectious agent is a phage. The antibiotic referred to in this application can be any agent that is bacteriostatic (capable of inhibiting the growth of a microorganism) or bactericidal (capable of killing a microorganism). Thus, in certain embodiments, the methods may comprise detection of resistance of a microorganism of interest in a sample to an antibiotic by contacting the sample with the antibiotic, and incubating the sample that has been contacted with antibiotic with an infectious agent that infects the microorganism of interest. This is distinct from those assays that detect the presence of genes (e.g., PCR) or proteins (e.g., antibody) that may confer antibiotic resistance, but do not test their functionality.

In certain embodiments, the methods may advantageously demonstrate functional resistance to an antibiotic for a microorganism of interest in a sample. For example, PCR allows for the detection of antibiotic-resistance genes; however, PCR is not able to distinguish between bacteria having functional antibiotic-resistance genes and those having non-functional antibiotic resistance-genes, thus, resulting in false-positive detection of antibiotic-resistant bacteria. The presently embodied methods, are capable of positively detecting bacteria with functional antibiotic-resistance genes, without positive detection of bacteria with non-functional antibiotic resistance genes.

In certain embodiments, the infectious agent comprises an indicator moiety. In other embodiments, the infectious agent comprises an indicator gene capable of expressing an indicator moiety. In some embodiments, the indicator moiety is an indicator protein product and the method may comprise detecting the indicator protein product, wherein positive detection of the indicator protein product indicates that the microorganism of interest is present in the sample and that the microorganism is resistant to the antibiotic. In some instances, the microorganism of interest is not isolated from the sample prior to testing for antibiotic resistance. In certain embodiments, the sample is an uncultured or unenriched sample. In some cases, the method of detecting antibiotic resistance can be completed within 5 hours. In some embodiments, the method comprises treatment with lysis buffer to lyse the microorganism infected with the infectious agent prior to detecting the indicator moiety.

In another aspect of the invention, the invention comprises a method of determining effective dose of an antibiotic in killing a microorganism comprising: (a) incubating each of one or more of antibiotic solutions separately with one or more samples comprising the microorganism, wherein the concentrations of the one or more of antibiotic solutions are different and define a range, (b) incubating the microorganisms in the one or more of samples with an infectious agent comprising an indicator gene, and wherein the infectious agent is specific for the microorganism of interest, and (c) detecting an indicator protein product produced by the infectious agent in the one or more of samples, wherein detection of the indicator protein product in one or more of the plurality of samples indicates the concentrations of antibiotic solutions used to treat the one or more of the one or more of samples are not effective, and the lack of detection of the indicator protein indicates the antibiotic is effective, thereby determining the effective dose of the antibiotic.

In certain embodiments, the invention may comprise a system. The system may contain at least some of the compositions of the invention. Also, the system may comprise at least some of the components for performing the method. In certain embodiments, the system is formulated as a kit. Thus, in certain embodiments, the invention may comprise a system for rapid detection of resistance to an antibiotic of a microorganism in a sample, comprising: a component for contacting the sample with the antibiotic, a component for incubating the sample with an infectious agent that is specific for the microorganism and comprises an indicator moiety; and a component for detecting the indicator moiety. The system may further comprise a component for lysing the microorganism before detecting the indicator moiety. In yet other embodiments, the invention comprises software for use with the methods or systems.

Embodiments of the methods and systems of the invention can be applied to detection of resistance to a variety of antibiotics, including but are not limited to cefoxitin, oxacillin ampicillin, vancomycin, penicillin, teicoplanin, and methicillin.

Embodiments of the methods and systems of the invention can be applied to detection and quantification of a variety of microorganisms (e.g., bacteria) in a variety of circumstances after being treated with an antibiotic, including but not limited to detection of pathogens from food, water, clinical and commercial samples.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. Known methods and techniques are generally performed according to conventional methods well known in the art and as described in various general and more specific references that are discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art.

The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

The term "solid support" or "support" means a structure that provides a substrate and/or surface onto which biomolecules may be bound. For example, a solid support may be an assay well (i.e., such as a microtiter plate or multi-well plate), or the solid support may be a location on a filter, an array, or a mobile support, such as a bead or a membrane (e.g., a filter plate or lateral flow strip).

The term "antibody" includes monoclonal antibodies, polyclonal antibodies, synthetic antibodies and chimeric antibodies, e.g., generated by combinatorial mutagenesis and phage display. The term "antibody" also includes mimetics or peptidomimetics of antibodies. Peptidomimetics are compounds based on, or derived from, peptides and proteins. The peptidomimetics of the present invention typically can be obtained by structural modification of a known peptide sequence using unnatural amino acids, conformational restraints, isosteric replacement, and the like. Fragments of antibodies may serve in place of antibodies in some embodiments. "Surface-specific antibodies" as used herein bind to molecules exposed on the outer surface of a specific microorganism.

As used herein, the term "free antibodies" refers to antibodies which are in solution and may move freely through a liquid; i.e., they are not initially bound to a solid support or otherwise constrained.

The term "detectable moiety" or "detectable biomolecule" or "reporter" or "indicator moiety" refers to a molecule that can be measured in a quantitative assay. "Indicator protein" or "indicator protein product" refers to a protein that can be measured in a quantitative assay. For example, an indicator moiety, e.g., an indicator protein, may comprise an enzyme that may be used to convert a substrate to a product that can be measured. An indicator moiety may be an enzyme that catalyzes a reaction that generates bioluminescent (e.g. luciferase), fluorescent emissions or products that can be detected by colorimetric means (e.g., alkaline phosphatase or beta-galactosidase). Alternatively, an indicator moiety may be a radioisotope that can be quantified, a fluorophore, or other detectable molecules that may be used.

As used herein, "bacteriophage" or "phage" includes one or more of a plurality of bacterial viruses. Here, "microscopic" means that the largest dimension is one millimeter or less. Phages are viruses that have evolved in nature to use bacteria as a means of replicating themselves. A phage does this by attaching itself to a bacterium and injecting its DNA (or RNA) into that bacterium, and inducing it to replicate the phage hundreds or even thousands of times. This is referred to as phage amplification.

As used herein, "late gene region" refers to a region of a viral genome that is transcribed late in the viral life cycle. The late gene region typically includes the most abundantly expressed genes (e.g., structural proteins assembled into the phage particle). Late genes are synonymous with class III genes and include genes with structure and assembly functions. For example, the late genes (synonymous with class III), are transcribed in T7, e.g., from 8 minutes after infection until lysis, class I (e.g., RNA polymerase) is early from 4-8 minutes, and class II from 6-15 minutes, so there is overlap in timing of II and III. A late promoter is one that is naturally located and active in such a late gene region.

As used herein, "cultured for enrichment," "culture for enrichment," or "culturing for enrichment" refers to traditional culturing, such as incubation in media favorable to propagation of microorganisms, and should not be confused with other possible uses of the word "enrichment," such as enrichment by removing the liquid component of a sample to concentrate the microorganism contained therein, or other forms of enrichment that do not include traditional facilitation of microorganism propagation. Culturing for enrichment for very short periods of time may be employed in some embodiments of methods described herein, but is not necessary and is for a much shorter period of time than traditional culturing for enrichment, if it is used at all. "Culturing for enrichment" as used herein exclude the type of selection of microorganisms resulted from incubating the sample comprising the microorganism with an antibiotic the resistance to which is the subject of the test. For example, the invention is used to detect the resistance to ampicillin of a microorganism in a sample, the step of contacting the sample with ampicillin is not considered to be a step of "culturing for enrichment."

As used herein, a "uncultured sample" refers to a sample that has not been cultured for enrichment.

As used herein "recombinant" refers to genetic (i.e., nucleic acid) modifications as usually performed in a laboratory to bring together genetic material that would not otherwise be found. This term is used interchangeably with the term "modified" herein.

As used herein "indicator infectious agent" refers to an infectious agent that is specific to the microorganism of interest and comprises an indicator moiety.

As used herein, the term "binding agent" refers to a molecule that can specifically and selectively bind to a second (i.e., different) molecule of interest. The interaction may be non-covalent, for example, as a result of hydrogen-bonding, van der Waals interactions, or electrostatic or hydrophobic interactions, or it may be covalent. The term "soluble binding agent" refers to a binding agent that is not associated with (i.e., covalently or non-covalently bound) to a solid support.

As used herein "fusion protein" refers to a non-native protein encoded by a non-native gene that is contiguous with a gene encoding a structural phage protein.

Microorganisms

Microorganisms of which antibiotic resistance can be detected by the methods and systems of the present invention include pathogens that are of commercial, medical or veterinary concern. Such pathogens include Gram-negative bacteria, Gram-positive bacteria, mycoplasmas, fungi, and yeast. Any microorganisms for which an infectious agent that is specific for the particular microbe has been identified can be detected by the methods of the present invention. Those skilled in the art will appreciate that there is no limit to the application of the present methods other than the availability of the necessary specific infectious agent/microbe pairs.

In some embodiments, the microorganism of interest is a bacterium. Bacterial cells detectable by the present invention include, but are not limited to, bacterial cells that are clinical, food, or water-borne pathogens. Bacterial cells detectable by the present invention include, but are not limited to, all species of *Staphylococcus*, including, but not limited to *S. aureus*, all species of *Salmonella*, all strains of *Escherichia coli*, including, but not limited to *E. coli* O157: H7, all species of *Listeria*, including, but not limited to *L. monocytogenes*, and all species of *Campylobacter*. Bacterial cells detectable by the present invention include, but are not limited to, bacterial cells that are pathogens of medical or veterinary significance. Such pathogens include, but are not limited to, *Bacillus* spp., *Bordetella pertussis*, *Campylobacter jejuni*, *Chlamydia pneumoniae*, *Clostridium perfringens*, *Enterobacter* spp., *Klebsiella pneumoniae*, *Mycoplasma pneumoniae*, *Salmonella typhi*, *Shigella sonnei*, and *Streptococcus* spp.

Additional microorganisms the antibiotic resistance of which can be detected using the claimed kits, systems, and methods can be selected from the group consisting of *Abiotrophia adiacens*, *Acinetobacter baumanii*, Actinomycetaceae, *Bacteroides*, *Cytophaga* and *Flexibacter* phylum, *Bacteroides fragilis*, *Bordetella pertussis*, *Bordetella* spp., *Campylobacter jejuni* and *C. coli*, *Candida albicans*, *Candida dubliniensis*, *Candida glabrata*, *Candida guilliermondii*, *Candida krusei*, *Candida lusitaniae*, *Candida parapsilosis*, *Candida tropicalis*, *Candida zeylanoides*, *Candida* spp., *Chlamydia pneumoniae*, *Chlamydia trachomatis*, *Clostridium* spp., *Corynebacterium* spp., *Crypococcus neoformans*, *Cryptococcus* spp., *Cryptosporidium parvum*, *Entamoeba* spp., Enterobacteriaceae group, *Enterococcus casseliflavus-flavescens-gallinarum* group, *Enterococcus faecalis*, *Enterococcus faecium*, *Enterococcus gallinarum*, *Enterococcus* spp., *Escherichia coli* and *Shigella* spp. group, *Gemella* spp., *Giardia* spp., *Haemophilus influenzae*, *Klebsiella pneumoniae*, *Legionella pneumophila*, *Legionella* spp., *Leishmania* spp., Mycobacteriaceae family, *Mycoplasma pneumoniae*, *Neisseria gonorrhoeae*, *Pseudomonas aeruginosa*, Pseudomonads group, *Staphylococcus aureus*, *Staphylococcus epidermidis*, *Staphylococcus haemolyticus*, *Staphylococcus hominis*, *Staphylococcus saprophyticus*, *Staphylococcus* spp., *Streptococcus agalactiae*, *Streptococcus pneumoniae*, *Streptococcus pyogenes*, and *Streptococcus* spp.

Sample

The sample may be environmental or food or water or medical or veterinary samples. Samples may be liquid, solid, or semi-solid. Samples may be swabs of solid surfaces. Samples may include environmental materials, such as water samples, or filters from air samples or aerosol samples from cyclone collectors. Samples may be taken from meat, poultry, fruit, vegetables, processed foods, milk, cheese, or other dairy products. Medical or veterinary samples include, but are not limited to, blood, sputum, cerebrospinal fluid, and fecal samples and different types of swabs.

Samples may be used directly in the detection methods of the present invention, without preparation, concentration, or dilution. For example, liquid samples, including but not limited to, milk and juices, may be assayed directly. Samples may be diluted or suspended in solution, which may include, but is not limited to, a buffered solution or a bacterial culture medium. A sample that is a solid or semi-solid may be suspending in a liquid by mincing, dissolving, mixing or macerating the solid in the liquid. A sample should be maintained within a pH range that promotes phage attachment to the host bacterial cell. A sample should also contain the appropriate concentrations of divalent and monovalent cations, including but not limited to $Na^+$, $Mg^{2+}$, and $K^+$. Preferably a sample is maintained at a temperature that maintains the viability of any pathogen cells contained within the sample.

Preferably, throughout detection assays, the sample is maintained at a temperature that maintains the viability of any pathogen cell present in the sample. During steps in which phages are attaching to bacterial cells, it is preferable to maintain the sample at a temperature that facilitates phage attachment. During steps in which phages are replicating within an infected bacterial cell or lysing such an infected cell, it is preferable to maintain the sample at a temperature that promotes phage replication and lysis of the host. Such temperatures are at least about 25 degrees Celsius (C), more preferably no greater than about 45 degrees C., most preferably about 37 degrees C. In some embodiments, the samples may be subjected to gentle mixing or shaking during phage attachment, replication, and/or cell lysis. In some embodiments, microorganisms are not isolated from samples prior to detection of antibiotic resistance.

Assays may include various appropriate control samples. For example, samples containing no infectious agent that is specific to the microorganism, or samples containing infectious agents but without microorganism, may be assayed as controls for background signal levels. In some cases, samples containing the microorganisms that have not been treated with the antibiotic, are assayed as controls for determining antibiotic resistance using the infectious agents.

In some embodiments, the sample signal is compared to the control signal to determine whether antibiotic-resistant microorganisms are present in the sample.

Indicator Infectious Agents

As described in more detail herein, the compositions, methods, systems and kits of the invention may comprise infectious agents for use in detection of such microorganisms. In some embodiments, detection is achieved through an indicator moiety specific for the microorganism of interest. For example, an infectious agent may comprise an indicator moiety, such as a gene encoding a soluble indicator. In some embodiments the indicator may be encoded by the infectious agent, such as a bacteriophage, and the bacteriophage is designated an indicator phage.

A variety of infectious agents may be used. In alternate embodiments, phages or mycobacteriophages (such as for TB and paraTB) may be used. For example, in an embodiment, where the microorganism of interest is a bacterium, the infectious agent may comprise a phage. In some embodiments, the phage may be a recombinant indicator phage. For example, compositions can include one or more wild-type or genetically modified infectious agents (e.g., phages) and one or more indicator genes. In some embodiments, compositions can include cocktails of different indicator phages that may encode and express the same or different indicator proteins.

As discussed herein, such phage may replicate inside of the bacteria to generate hundreds of progeny phage. Detection of the indicator gene inserted into the phage can be used as a measure of the bacteria in the sample. *S. aureus* phages include, but are not limited to phage K, SA1, SA2, SA3, SA11, SA77, SA 187, Twort, NCTC9857, Ph5, Ph9, Ph10, Ph12, Ph13, U4, U14, U16, and U46. Well-studied phages of *E. coli* include T1, T2, T3, T4, T5, T7, and lambda; other *E. coli* phages available in the ATCC collection, for example, include phiX174, S13, Ox6, MS2, phiV1, fd, PR772, and ZIK1. Alternatively, natural phage may be isolated from a variety of environmental sources. A source for phage isolation may be selected based on the location where a microorganism of interest is expected to be found.

As described above for the compositions of the invention, the phage is derived from T7, T4, T4-like, phage K, MP131, MP115, MP112, MP506, MP87, Rambo, or another naturally occurring phage having a genome with at least 99, 98, 97, 96, 95, 94, 93, 92, 91, 90, 89, 88, 87, 86, 85, 84, 83, 82, 81, 80, 79, 78, 77, 76, 75, 74, 73, 72, 71, or 70% homology to phages disclosed above. In some aspects, the invention comprises a recombinant phage comprising an indicator gene inserted into a late gene region of the phage. In some embodiments, the phage is a T4-like phage. In one embodiment, the recombinant phage is derived from phage K. In certain embodiments, the recombinant phage is highly specific for a particular bacterium. For example, in certain embodiments, the recombinant phage is highly specific for *E. coli* O157:H7. In an embodiment, the recombinant phage can distinguish *E. coli* O157:H7 in the presence of more than 100 other types of bacteria.

In some embodiments of the invention, a composition may comprise a recombinant phage having an indicator gene inserted into the phage genome. In certain embodiments, the indicator gene may be inserted into a late gene region of the phage and is only expressed during phage infection and replication. In a recombinant phage the late gene region may be a class III gene region. Insertion of the indicator gene into the late class III gene region may ensure that the indicator gene is expressed in high quantities upon replication in the bacterium and thus increase the sensitivity of the assay. As described in more detail below, in certain embodiments, the indicator gene encodes an indicator protein product that is not a fusion protein. For example, in certain embodiments, expression of the indicator gene during phage replication following infection of a host bacterium results in a soluble indicator protein product.

In some embodiments, the indicator phage is derived from a natural phage isolated from the environment, such as T4-like phages or other phages as described in the Examples. In some embodiments, an indicator bacteriophage is derived from phage K, T7, T4 or another similar phage. An indicator bacteriophage may also be derived from Twort-like, phage K-like, T4-like, T7-like, ViI, ViI-like, or *Staphylococcus*-specific bacteriophage. The genetic modifications may avoid deletions of wild-type genes and thus remain more similar to the wild-type infectious agent than many commercially available phage, e.g. T7SELECT®415. Such naturally derived phage may be more specific for bacteria that are found in the environment than phage that are commercially available and as such, genetically distinct from phage found in the environment.

Moreover, phage genes thought to be nonessential may have unrecognized function. For example, an apparently nonessential gene may have an important function in elevating burst size with subtle cutting, fitting, or trimming functions in assembly. As such, deleting genes to insert an indicator may be detrimental. Most phages can package a DNA that is a few percent larger than their natural genome. With this consideration, a smaller indicator gene may be a more appropriate choice for modifying a phage, especially one with a smaller genome. OpLuc and NANOLUC® proteins are only about 20 kDa (approximately 500-600 bp to encode), while FLuc is about 62 kDa (approximately 1,700 bp to encode). For comparison, the genome of T7 is around 40 kbp, while the T4 genome is about 170 kbp. The genome of *S. aureus*-specific phage, phage K, is about 148 kbp. Additionally, luciferase proteins are highly luminescent, thus, allowing for increased detection with lower amounts of indicator protein product.

In some embodiments, the indicator gene may be inserted into an untranslated region to avoid disruption of functional genes, leaving wild-type phage genes intact, which may lead to greater fitness when infecting non-laboratory strain bacteria. Additionally, stop codons at all three reading frames may help to increase expression by reducing read-through, also known as leaky expression. This strategy may also eliminate the possibility of a fusion protein being made at low levels, which would manifest as background signal (e.g., luciferase) that cannot be separated from the phage.

An indicator gene may express a variety of biomolecules. The indicator gene is a gene that expresses a detectable product or an enzyme that produces a detectable product. For example, in one embodiment the indicator gene encodes a luciferase enzyme. Various type of luciferase may be used. In alternate embodiments, and as described in more detail herein, the luciferase is one of Oplophorus luciferase, or Firefly luciferase. In some embodiments, the indicator gene is a genetically modified luciferase gene, such as NANO-LUC®.

Thus, in some embodiments, the present invention comprises a modified phage comprising a non-phage indicator gene in the late (class III) gene region. In some embodiments, the non-native indicator gene is under the control of a late promoter. Using a viral late gene promoter ensures the reporter gene (e.g., luciferase) is not only expressed at high levels, like viral capsid proteins, but also does not shut down like endogenous bacterial genes or early viral genes.

In some embodiments, the late promoter is a phage K, T4-, T7-, or ViI-like promoter, or another phage promoter similar to that found in the natural phage without genetic modification. The late gene region may be a class III gene region, and the phage may be derived from phage K, T7, T4, T4-like, or another natural phage having a genome with at least 70, 75, 80, 85, 90 or 95% homology to phage K, T7, T4, T4-like, ViI, ViI-like phages. In preferred embodiments, the indicator gene encodes an indicator protein product that is not a fusion protein.

In some embodiments, expression of the indicator gene in progeny bacteriophage following infection of host bacteria results in a free, soluble protein product that is not part of the phage structure. In some embodiments, the non-native indicator gene is not contiguous with a gene encoding a structural phage protein and therefore does not yield a fusion protein. Unlike systems that employ a fusion of a detection moiety to the capsid protein (i.e., a fusion protein), some embodiments of the present invention express a soluble indicator or reporter (e.g., soluble luciferase). In some embodiments, the indicator or reporter is ideally free of the bacteriophage structure. That is, the indicator or reporter is not attached to the phage structure. As such, the gene for the indicator or reporter is not fused with other genes in the recombinant phage genome. This may greatly increase the sensitivity of the assay (down to a single bacterium), and simplifies the assay, allowing the assay to be completed in less than an hour for some embodiments, as opposed to several hours due to additional purification steps required with constructs that produce detectable fusion proteins. Further, fusion proteins may be less active than soluble proteins due, e.g., to protein folding constraints that may alter the conformation of the enzyme active site or access to the substrate.

Genetic modifications to infectious agents may include insertions, deletions, or substitutions of a small fragment of nucleic acid, a substantial part of a gene, or an entire gene. In some embodiments, inserted or substituted nucleic acids comprise non-native sequences. A non-native indicator gene may be inserted into a phage genome such that it is under the control of a phage promoter. In some embodiments, the non-native indicator gene is not part of a fusion protein. That is, in some embodiments, a genetic modification may be configured such that the indicator protein product does not comprise polypeptides of the natural phage. In some embodiments, the indicator protein product is soluble. In some embodiments, the invention comprises a method for detecting a microorganism of interest comprising the step of incubating a test sample with such a modified phage.

In some cases, the indicator moiety is an indicator protein that is encoded by an indicator gene in the infectious agent such that expression of the indicator gene during phage replication following infection of the microorganism of interest results in a soluble indicator protein product; wherein positive detection of the indicator protein indicates that the microorganism of interest in the sample is resistant to the antibiotic. In some cases, the indicator moiety is an enzyme that produces a detectable product and the signal derived from the detectable product corresponds to the amount of indicator moiety. In some embodiments, the indicator gene encodes a protein that emits an intrinsic signal, such as a fluorescent protein (e.g., green fluorescent protein or others). The indicator may emit light and/or may be detectable by a color change. In some embodiments, the indicator gene encodes an enzyme (e.g., luciferase) that interacts with a substrate to generate signal. In certain embodiments, the indicator gene does not encode a fusion protein. Thus, in certain embodiments, expression of the indicator gene during phage replication following infection of host bacteria results in a soluble indicator protein product. In some cases detection of the indicator moiety does not involve an antibody specific to the infectious agent.

In some embodiments, the indicator phage encodes a detectable enzyme. The indicator may emit light and/or may be detectable by a color change. Various appropriate enzymes are commercially available, such as alkaline phosphatase (AP), horseradish peroxidase (HRP), or luciferase (Luc). In some embodiments, these enzymes may serve as the indicator moiety. In some embodiments, Firefly luciferase is the indicator moiety. In some embodiments, Oplophorus luciferase is the indicator moiety. In some embodiments, NANOLUC® is the indicator moiety. Other engineered luciferases or other enzymes that generate detectable signals may also be appropriate indicator moieties.

Also, the use of a free, soluble detection moiety eliminates the need to isolate contaminating parental phage from the lysate of the infected sample cells. With a fusion protein system, any phage used to infect sample cells would have the detection moiety attached, and would be indistinguishable from the progeny phage also containing the detection moiety. As detection of sample bacteria relies on the detection of newly created (de novo synthesized) detection moiety, the additional steps of separating old (parental) moieties from newly created (progeny phage) moieties required when using fusion constructs are not necessary. Typically, separation of parental moieties from progeny moieties may be accomplished by washing the infected cells multiple times, prior to the completion of the phage life cycle, inactivating excess parental phage after infection by physical or chemical means, and/or chemically modifying the parental phage with a binding moiety (such as biotin), which can then be bound and separated (such as by streptavidin-coated sepharose beads). However, even with all these attempts at isolation, parental phage typically remain when a high multiplicity of infection (MOI) is used to assure infection of a low number of sample cells, thus, creating background signal that may obscure detection of signal from infected cell progeny phage.

By contrast, the free, soluble detection moiety expressed in some embodiments of the present invention, purification of the parental phage from the final lysate is unnecessary, as the parental phage will not have any detection moiety attached. Thus, any detection moiety present after infection must have been created de novo, indicating the presence of an infected bacterium or bacteria. To take advantage of this benefit, the production and preparation of parental phage may include purification of the phage from any free detection moiety produced during the production of parental phage in bacterial culture. Standard phage purification techniques may be employed to purify some embodiments of phage according to the present invention, such as sucrose density gradient centrifugation, cesium chloride isopycnic density gradient centrifugation, HPLC, size exclusion chromatography, and dialysis or derived technologies (such as Amicon brand concentrators—Millipore, Inc.). The Examples herein describe the use of cesium chloride isopycnic ultracentrifugation as part of the preparation of recombinant phage of the invention so as to separate parental phage particles from contaminating luciferase protein produced upon propagation of the phage in the bacteria stock. In this way, the recombinant phage of the invention is substantially free of any luciferase generated during production in the bacteria. Removal of residual luciferase present in the phage stock can substantially reduce background signal seen when the recombinant phage are incubated with a test sample.

In some embodiments of modified phage, the late promoter (class III promoter, e.g., from phage K or T7 or T4) has high affinity for RNA polymerase of the same native phage (e.g., phage K or T7 or T4, respectively) that transcribes genes for structural proteins assembled into the phage particle. These proteins are the most abundant proteins made by the phage, as each phage particle comprises dozens or hundreds of copies of these molecules. The use of a viral late promoter can ensure optimally high level of expression of the luciferase detection moiety. The use of a late viral promoter derived from, specific to, or active under the original wild-type phage the indicator phage is derived from (e.g., the phage K or T4 or T7 late promoter with a phage K- or T4- or T7-based system) can further ensure optimal expression of the detection moiety. The use of a standard bacterial (non-viral/non-phage) promoter may in some cases be detrimental to expression, as these promoters are often down-regulated during phage infection (in order for the phage to prioritize the bacterial resources for phage protein production). Thus, in some embodiments, the phage is preferably engineered to encode and express at high levels a soluble (free) indicator moiety, which does not limit expression to the number of subunits of a phage structural component.

Embodiments employing modified phage of the invention may allow rapid detection of specific bacterial strains, with total assay times as fast as 45 minutes-2.0 hours. The amount of time required may be somewhat shorter or longer depending on the strain of phage and the strain of bacteria to be detected in the assay.

The strategy of using indicator phage that produce soluble luciferase employs phage (e.g., phage K) engineered to express a soluble luciferase during replication instead of a capsid protein-luciferase fusion. Expression of luciferase is driven by a viral capsid promoter (e.g., the Soc promoter in T4 phage), yielding high expression. Parental phage will be free of luciferase, so any luciferase detected in the assay must come from replication of progeny phage released from the bacterial cells. Thus, there is no need to separate out the parental phage and the progeny phage.

Antibiotics and Antibiotic Resistance

The methods disclosed herein can be used to detect whether a microorganism of interest is susceptible or resistant to an antibiotic. A particular antibiotic may be specific for the type of microorganism it kills or inhibits; the antibiotic kills or inhibits the growth of microorganisms that are sensitive to the antibiotic and does not kill or inhibit the growth of microorganisms that are resistant to the antibiotic. In some cases, a previously sensitive microbial strain may become resistant. Resistance of microorganisms to antibiotics can be mediated by a number of different mechanisms. For example, some antibiotics disturb cell wall synthesis in a microorganism; resistance against such antibiotics can be mediated by altering the target of the antibiotic, namely a cell wall protein. In some cases, bacteria create resistance to an antibiotic by producing compounds capable of inactivating the antibiotic before reaching the bacteria. For example, some bacteria produce beta-lactamase, which is capable of cleaving the beta-lactam of penicillin or/and carbapenems, thus, inactivating these antibiotics. In some cases, the antibiotic is removed from the cell before reaching the target by a specific pump. An example is the RND transporter. In some cases, some antibiotics act by binding to ribosomal RNA (rRNA) and inhibit protein biosynthesis in the microorganism. A microorganism resistant to such antibiotic may comprise a mutated rRNA having a reduced binding capability to the antibiotic but having an essentially normal function within the ribosome. In other cases, bacteria harbor a gene that is capable of conferring resistance. For example, some MRSA harbor the mecA gene. The mecA gene product prevents the ring-like structure of certain antibiotics from binding to the enzymes that assist in bacterium cell wall formation. Therefore, antibiotics, including beta-lactams, are unable to inhibit cell wall synthesis in these bacteria. Some bacteria harbor antibiotic resistance genes that are non-functional, possibly due to mutation of the gene or regulation, which may be falsely detected as antibiotic-resistant with conventional nucleic acid methods, such as PCR, but not detected by functional methods, such as plating or culturing with antibiotics or this method.

Non-limiting examples of antibiotics that can be used in the invention include aminoglycosides, carbacephems, carbapenems, cephalosporins, glycopeptides, macrolides, monobactams, penicillin, beta-lactam antibiotic, quinolones, bacitracin, sulfonamides, tetracyclines, streptogramines, chloramphenicol, clindamycin, and lincosamide, cephamycins, lincomycins, daptomycin, oxazolidinone, and glycopeptide antibiotic.

Methods of Using Infectious Agents for Detecting Antibiotic Resistance of the Microorganisms or Detecting Antibiotic-Resistant Bacteria As noted herein, in certain embodiments, the invention may comprise methods of using infectious particles for detecting resistance of microorganisms to an antibiotic or, stated another way, for detecting the efficacy of an antibiotic against a microorganism. In another embodiment, the invention comprises methods for selecting an antibiotic for treatment of an infection. Additionally, the methods may comprise methods for detecting antibiotic-resistant bacteria in a sample. The methods of the invention may be embodied in a variety of ways.

The method may comprise contacting the sample comprising the microorganism with the antibiotic and an infectious agent as described above. In some embodiments, the disclosure provides a method of determining effective dose of an antibiotic in killing or inhibiting the growth of a microorganism comprising: (a) incubating each of one or more of antibiotic solutions separately with one or more samples comprising the microorganism, wherein the concentrations of the one or more antibiotic solutions are different and define a range, (b) incubating the microorganisms in the one or more of samples with an infectious agent comprising an indicator gene, and wherein the infectious agent is specific for the microorganism of interest, and (c) detecting an indicator protein product produced by the infectious agent in the one or more of samples, wherein detection of the indicator protein product in one or more of the plurality of samples indicates the concentrations of antibiotic solutions used to treat the one or more of the one or more of samples are not effective, and the lack of detection of the indicator protein indicates the antibiotic is effective, thereby determining the effective dose of the antibiotic.

In some embodiments, the antibiotic and the infectious agent are simultaneously added to the sample such that the sample contacts with both antibiotic and the infectious agent. In other embodiments, the antibiotic and the infectious agent are added sequentially, e.g., the sample is contacted with the antibiotic before the sample is contacted with the infectious agent. In certain embodiments, the method may comprise incubating the sample with the antibiotic for a period time before contacting the sample with the infectious agent. The incubation time may vary depending on the nature of the antibiotic and the microorganism, for example based on the doubling time of the microorganism. In some embodiments, the incubation time is less than 24 hours, less than 18 hours, less than 12 hours, less than 6 hours, less than 5 hours, less than 4 hours, less than 3 hours, less than 2 hours, less than 1 hour, less than 45 min, less than 30 min, less than 15 min, less than 10 min or less than 5 min. The incubation time of microorganism with the infectious agent may also vary depending on the life cycle of the particular infectious agent, in some cases, the incubation time is less than 4 hours, less than 3 hours, less than 2 hours, less than 1 hour, less than 45 min, less than 30 min, less than 15 min, less than 10 min or less than 5 min. Microorganisms that are resistant to the antibiotic will survive and may multiply, and the infectious agent that is specific to the microorganism will replicate; conversely, microorganisms that are sensitive to the antibiotic will be killed and thus the infectious agent will not replicate. The infectious agent according to this method comprises an indicator moiety, the amount of which corresponds to the amount of the microorganisms present in the sample that have been treated with the antibiotic. Accordingly, a positive detection of the indicator moiety indicates the microorganism is resistant to the antibiotic.

In some embodiments, the methods may be used to determine whether an antibiotic-resistant microorganism is present in a clinical sample. For example, the methods may be used to determine whether a patient is infected with *Staphylococcus aureus* that are resistant or susceptible to a particular antibiotic. A clinical sample obtained from a patient may then be incubated with an antibiotic specific for *S. aureus*. The sample may then be incubated with recombinant phage specific for *S. aureus* for a period of time. In samples with *S. aureus* resistant to the antibiotic, detection of the indicator protein produced by the recombinant phage will be positive. In samples with *S. aureus* susceptible to the antibiotic, detection of the indicator protein will be negative. In some embodiments, methods for detection of antibiotic resistance may be used to select an effective therapeutic to which the pathogenic bacterium is susceptible.

In certain embodiments the total time required for detection is less than 6.0 hours, 5.0 hours, 4.0 hours, 3.0 hours, 2.5 hours, 2.0 hours, 1.5 hours, or less than 1.0 hour. The total time required for detection will depend on the bacteria of interest, the type of phage, and antibiotic being tested.

Optionally, the method further comprises lysing the microorganism before detecting the indicator moiety. Any solution that can lyse the microorganism can be used. In some cases, the lysis buffer may contain non-ionic detergents, chelating agents, enzymes or proprietary combinations of various salts and agents. Lysis buffers are also commercially available from Promega, Sigma-Aldrich, or Thermo-Fisher. Experiments suggest that infected unlysed cells may be detectable upon addition of luciferase substrate in some embodiments. Presumably, luciferase may exit cells and/or luciferase substrate may enter cells without complete cell lysis. Thus, for embodiments utilizing the spin filter system, where only luciferase released into the lysate (and not luciferase still inside intact bacteria) is analyzed in the luminometer, lysis is required for detection. However, for embodiments utilizing filter plates or 96-well plates with phage-infected sample in solution or suspension as described below, where intact and lysed cells may be directly assayed in the luminometer, lysis may not be necessary for detection. Thus, in some embodiments, the method of detecting antibiotic resistance does not involve lysing the microorganism.

A surprising aspect of embodiments of the assays is that the step of incubating the microorganism in a sample with infectious agent only needs to be long enough for a single life cycle of the infectious agent, e.g., a phage. The amplification power of using phage was previously thought to require more time, such that the phage would replicate for several cycles. A single replication of indicator phage may be sufficient to facilitate sensitive and rapid detection according to some embodiments of the present invention. Another surprising aspect of the embodiments of the assays is that high concentrations of phage utilized for infecting test samples (i.e., high MOI) have successfully achieved detection of very low numbers of antibiotic resistant target microorganisms that have been treated with antibiotic. Factors, including the burst size of the phage, can affect the number of phage life cycles, and therefore, amount of time needed for detection. Phage with a large burst size (approximately 100 PFU) may only require one cycle for detection, whereas phage with a smaller burst size (e.g., 10 PFU) may require multiple phage cycles for detection. In some embodiments, the incubation of phage with a test sample need only be long enough for a single phage life cycle. In other embodiments, the incubation of phage with a test sample is for an amount of time greater than a single life cycle. The phage concentration for the incubating step will vary depending on the type of phage used. In some embodiments, the phage concentration for this incubating step is greater than $1.0 \times 10^5$, greater than $1.0 \times 10^6$, greater than $1.0 \times 10^7$, or greater than $1.0 \times 10^8$ PFU/mL. Success with such high concentrations of phage is surprising because such large numbers of phage were previously associated with "lysis from without," which killed target cells immediately and thereby prevented generation of useful signal from earlier phage assays. It is possible that the purification of the phage stock described herein helps to alleviate this problem (e.g., purification by cesium chloride isopycnic density gradient ultracentrifugation), because in addition to removing any contaminating luciferase associated with the phage, this purification may also remove ghost particles (particles that have lost DNA). The ghost particles can lyse bacterial cells via "lysis from without," killing the cells prematurely and thereby preventing generation of indicator signal. Electron microscopy demonstrates that a crude recombinant phage lysate (i.e., before cesium chloride purification) may have greater than 50% ghosts. These ghost particles may contribute to premature death of the microorganism through the action of many phage particles puncturing the cell membrane. Thus ghost particles may have contributed to previous problems where high PFU concentrations were reported to be detrimental.

Any of the indicator moieties as described in this disclosure may be used for detecting the viability of microorganisms after antibiotic treatment, thereby detecting antibiotic resistance. In some embodiments, the indicator moiety associated with the infectious agent may be detectable during or after replication of the infectious agent. For example, as described above, in some cases, the indicator moiety may be a protein that emits an intrinsic signal, such as a fluorescent protein (e.g., green fluorescent protein or others). The indicator may generate light and/or may be detectable by a color change. In some embodiments, a luminometer may be used to detect the indicator (e.g., luciferase). However, other machines or devices may also be used. For example, a spectrophotometer, CCD camera, or CMOS camera may detect color changes and other light emissions.

In some embodiments, exposure of the sample to antibiotic may continue for 5 minutes or more and detection at various time points may be desirable for optimal sensitivity. For example, aliquots of a primary sample treated with antibiotic can be taken at different time intervals (e.g., at 5 minutes, 10 minutes, or 15 minutes). Samples from varying time interval may then be infected with phage and indicator moiety measured following the addition of substrate.

In some embodiments, detection of the signal is used to determine antibiotic resistance. In some embodiments, the signal produced by the sample is compared to an experimentally determined value. In further embodiments, the experimentally determined value is a signal produced by a control sample. In some embodiments, the background threshold value is determined using a control without microorganisms. In some embodiments, a control without phage or without antibiotic, or other control samples may also be used to determine an appropriate threshold value. In some embodiments, the experimentally determined value is a background threshold value calculated from an average background signal plus standard deviation of 1-3 times the average background signal, or greater. In some embodiments, the background threshold value may be calculated from average background signal plus standard deviation of 2 times the average background signal. In other embodiments, the background threshold value may be calculated from the average background signal times some multiple (e.g., 2 or 3). Detection of a sample signal greater than the background threshold value indicates the presence of one or more antibiotic-resistant microorganisms in the sample. For example, the average background signal may be 250 RLU. The threshold background value may be calculated by multiplying the average background signal (e.g., 250) by 3 to calculate a value of 750 RLU. Samples with bacteria having a signal value greater than 750 RLU are determined to be positive for containing antibiotic-resistant bacteria.

Alternatively, the experimentally determined value is the signal produced by a control sample. Assays may include various appropriate control samples. For example, samples containing no infectious agent that is specific to the microorganism, or samples containing infectious agents but without microorganism, may be assayed as controls for background signal levels. In some cases, samples containing the microorganisms that have not been treated with the antibiotic, are assayed as controls for determining antibiotic resistance using the infectious agents.

In some embodiments, the sample signal is compared to the control signal to determine whether antibiotic-resistant microorganisms are present in the sample. Unchanged detection of the signal as compared to a control sample that is contacted with the infectious agent but not with the antibiotic indicates the microorganism is resistant to the antibiotic, and reduced detection of the indicator moiety as compared to a control sample that is contacted with infectious agent but not with antibiotic indicates the microorganism is susceptible to the antibiotic. Unchanged detection refers to the detected signal from a sample that has been treated with the antibiotic and infectious agent is at least 80%, at least 90%, or at least 95% of signal from a control sample that has not been treated with the antibiotic. Reduced detection refers to the detected signal from a sample that has been treated with the antibiotic and infectious agent is less than 80%, less than 70%, less than 60%, less than 50%, less than 40%, or at least 30% of signal from a control sample that has not been treated with the antibiotic.

Optionally, the sample comprising the microorganism of interest is an uncultured sample. Optionally, the infectious agent is a phage and comprises an indicator gene inserted into a late gene region of the phage such that expression of the indicator gene during phage replication following infection of host bacteria results in a soluble indicator protein product. Features of each of the compositions used in the methods, as described above, can be also be utilized in the methods for detecting antibiotic resistance of the microorganism of interest.

Also provided herein is a method of determining the effective dose of an antibiotic for killing a microorganism. In some embodiments, the antibiotic is effective at killing *Staphylococcus* species. For example, the antibiotic may be cefoxitin, which is effective against most methicillin-sensitive *S. aureus* (MSSA). Typically, one or more antibiotic solutions having different concentrations are prepared such that the different concentrations of the solutions define a range. In some cases, the concentration ratio of the least concentrated antibiotic solution to the most concentrated antibiotic solution ranges from 1:2 to 1:50, e.g., from 1:5 to 1:30, or from 1:10 to 1:20. In some cases, the lowest concentration of the one or more antibiotic solution is at least 1 µg/mL, e.g., at least 2 µg/mL, at least 5 µg/mL at least 10 µg/mL, at least 20 µg/mL, at least 40 µg/mL, at least 80 µg/mL, or at least 100 µg/mL. Each of the one or more antibiotic solutions is incubated with one aliquot of the sample comprising the microorganism of interest. In some cases, the infectious agent that is specific to the microorganism and comprises an indicator moiety is added simultaneously with the antibiotic solutions. In some cases, the aliquots of sample are incubated with the antibiotic solutions for a period of time before the addition of the infectious agent. The indicator moiety can be detected, and positive detection indicates that the antibiotic solution is not effective and negative detection indicates the antibiotic solution is effective and the concentration of the antibiotic solution is an effective dose. Accordingly, in some embodiments, the method of determining effective dose of an antibiotic in killing a microorganism of interest comprises incubating each of one or more antibiotic solutions separately with a microorganism of interest in a sample, wherein the concentrations of the one or more antibiotic solutions are different and define a range; incubating the microorganism in the one or more samples with an infectious agent comprising an indicator moiety; detecting the indicator moiety of the infectious agent in the one or more samples, wherein positive detection of the indicator moiety in one or more of the one or more samples indicates the concentrations of antibiotic solutions used to treat the one or more of the one or more samples are not effective, and the lack of detection of the indicator protein indicates the antibiotic is effective, thereby determining the effective dose of the antibiotic. In some embodiments, two or more antibiotic solutions are tested and the concentration ratio of the least concentrated solution and the most concentrated solution in the one or more antibiotic solutions ranges from 1:2 to 1:50, e.g., from 1:5 to 1:30, or from 1:10 to 1:20. In some cases, the lowest concentration of the one or more antibiotic solution is at least 1 µg/mL, e.g., at least 2 µg/mL, at least 5 µg/mL at least 10 µg/mL, at least 20 µg/mL, at least 40 µg/mL, at least 80 µg/mL, or at least 100 µg/mL.

In some embodiments, the present invention comprises methods for detecting antibiotic-resistant microorganisms in the presence of antibiotic-sensitive microorganisms. In certain instances, detection of antibiotic-resistant bacteria can be used to prevent the spread of infection in healthcare settings. In some embodiments, patients in a healthcare setting may be monitored for colonization of antibiotic-resistant bacteria. Preventative measures may then be implemented to prevent the spread of antibiotic-resistant bacteria.

In some embodiments of methods for detecting antibiotic resistant microorganisms, samples may contain both antibiotic-resistant and antibiotic-sensitive bacteria. For example, samples may comprise both MRSA and MSSA. In some embodiments, MRSA can be detected in the presence of MSSA without the need for isolation of MRSA from the sample. In the presence of antibiotic, MSSA does not generate a signal above the threshold value, but MRSA present in the sample are capable of producing a signal above the threshold value. Thus, if both are present within a sample, a signal above the threshold value indicates the presence of an antibiotic-resistant strain (e.g. MRSA).

Capture of Microorganisms Before Incubation with Antibiotic and Infectious Agent In some embodiments, the present invention comprises methods and systems that do not require a step for capturing microorganisms. Other embodiments allow physical isolation of microorganisms from a sample before the antibiotic treatment. In certain embodiments, the method may comprise a step for capturing the microorganism from the sample on a solid support before contacting the microorganism from the sample with the antibiotic and/or the infectious agent. In some embodiments, capture steps can be performed simultaneously with or after contacting antibiotic. In some embodiments, the method comprises contacting the microorganism from the sample with the antibiotic before capturing the microorganisms from the sample on a solid support. This would reduce the number of antibiotic sensitive microorganisms and thus advantageously reduce the background. In some cases, the method comprises immobilizing the recombinant phage on a solid support and contacting the mixture comprising the sample and the antibiotics with the phage on the support and detecting the indicator moiety. In some cases, the indicator moiety is expressed and detectable only during phage infection and replication.

In various embodiments of the methods of the invention, the antibiotic resistance of the microorganism may be detected without any purification of the microorganisms from a sample. For example, in certain embodiments, a sample containing one or a few microorganisms of interest may be applied directly to an assay container such as a spin column, a microtiter well, or a filter and the assay is conducted in that assay container. Various embodiments of such assays are disclosed herein.

In some embodiments, the method may include contacting a microorganism captured on a solid support (e.g., a magnetic bead or a filter substrate) with the antibiotic and a plurality of the specific infectious agent (e.g., indicator phage) and allowing the infectious agent to bind and infect the microorganism. In other embodiments, capture of the microorganism is not necessary for detection. A variety of solid supports may be used. In certain embodiments, the solid support may comprise a multi-well plate, a filter, a bead, or a lateral flow strip, a filter strip, filter disc, or filter paper, or thin films designed for culturing cells (e.g., PETRIFILM® by 3M). Other solid supports may also be appropriate. For example, in some embodiments the test sample microorganism may be captured by binding to the surface of a plate, or by filtering the sample through a bacteriological filter (e.g., 0.45 μm pore size spin filter or plate filter). In some embodiments, antibiotic is added directly on the filter. In further embodiments, captured microorganisms are enriched and then incubated with an infectious agent. In an embodiment, the microorganism captured on the filter or plate surface is subsequently washed one or more times to remove excess unbound infectious agent. In an embodiment, medium (e.g., Luria-Bertani also called LB broth herein) is added for further incubation time, to allow replication of phage and high-level expression of the gene encoding the indicator moiety.

The microorganism of interest may be purified from the sample by using a binding agent. Optionally, in certain embodiments, the capturing step further comprises binding the microorganism of interest with a capture antibody that recognizes the microorganism. The antibody may be used in conjunction with the solid support. For example, in certain embodiments, the capture antibody facilitates binding of the microorganism to the solid support. Optionally, the capture antibody recognizes a surface antigen of the microorganism. In preferred embodiments, the surface-specific antibodies that recognize the microbial surface antigens of a particular microorganism (e.g., $E.\ coli$ O157:H7) do not recognize other similar microorganisms (e.g., $E.\ coli$ B). In some embodiments, capture antibodies may be conjugated to a chemical moiety that binds with another binding agent attached to a solid support (e.g. beads or a plate surface). For example, in some embodiments, the capture antibody may be biotinylated to facilitate binding to streptavidin bound to a solid support. In some embodiments, the solid support comprises magnetic beads and optionally these beads are coated with a chemical moiety that binds the capture antibody. In other embodiments, a solid support comprises a plate surface or the surfaces of a multi-well plate (e.g., an ELISA plate). For example, an ELISA plate may be coated with an antibody that specifically recognizes the microorganism of interest. Antibodies demonstrating specific recognition of surface antigens on a wide variety of bacteria or other microorganisms are available commercially from a number of sources, such as Kirkegaard & Perry Laboratories, Inc. (KPL) or Abcam.

In some embodiments, the present invention utilizes the physical size of the microorganism to capture it on a solid support. In some embodiments, the solid support is a filter. For example, filtering a sample through a bacteriological filter (e.g., 0.45 μm pore size spin filter) allows smaller substances to pass through while retaining intact bacteria. Alternatively, a plate filter may be used to capture a microorganism, or a variety of other filter devices may be used (e.g., 96-well filter plate). For example, the method may include the step of collecting the microorganism on a solid support such as by filtering a sample through a bacteriological filter. After size-based capture, the antibiotic and the indicator infectious agent can be added, sequentially or simultaneously, as described above, to identify antibiotic resistance of the microorganism. Other methods of isolating the microorganisms in the sample may be used, such as those described in US Patent Publication No. 2015/0218616, which is incorporated herein by reference.

Alternatively, in some embodiments the capturing step may be based on other features of the microorganism of interest, such as size. In embodiments utilizing size-based capture, the solid support may be a spin column filter. In some embodiments, the solid support comprises a 96-well filter plate. Or, the solid support for capture may be a location on an array, or a mobile support, such as a bead.

In some embodiments, the capture antibody is biotinylated such that it facilitates subsequent binding of cell-antibody complexes to magnetic streptavidin beads. The biotin on the antibody can bind tightly to the streptavidin on the magnetic bead. Or the capture antibody may be conjugated to another protein or other molecule, which facilitates capture on beads or another solid support. Such embodiments may provide increased sensitivity, particularly where the initial sample volume is large. Thus, the method may comprise the steps of attaching a plurality of binding agents that can specifically bind to a surface antigen on the microorganism of interest, which thereby facilitates binding to a capture solid support.

Sensitivity

In contrast to assays known in the art, detection of antibiotic resistance of a microorganism is highly sensitive and may be completed without the need for culturing the sample as a way to increase the population of the microorganisms. This is in part due to the ability of a single microorganism to bind a large number of specific infectious agents, e.g., phages. Following infection and replication of the phage, target microorganisms may be detected via an indicator moiety produced during phage replication.

Thus, in certain embodiments, the method may detect antibiotic resistance of a microorganism in a sample that comprises ≤10 cells of the microorganism (i.e., 1, 2, 3, 4, 5, 6, 7, 8, 9, 10 microorganisms). For example, in certain embodiments, the recombinant phage is highly specific for $E.\ coli$ O157:H7. In an embodiment, the recombinant phage can distinguish $E.\ coli$ O157:H7 in the presence of more than 100 other types of bacteria. In certain embodiments, the recombinant phage can be used to detect antibiotic resistance by detection of a single bacterium of the specific type in the sample that has been treated with the antibiotic. In certain embodiments, the recombinant phage detects the presence of as few as 2, 3, 4, 5, 6, 7, 8, 9, 10, 15, 20, 30, 40, 50, 60, 70, 80, 90, or 100 of the specific bacteria in the sample that has been contacted with antibiotic.

The sensitivity of the method of detecting antibiotic resistance as disclosed herein may be further increased by washing the captured and infected microorganisms prior to incubation with the antibiotic. Additionally, captured microorganisms may be washed following incubation with antibiotic and the infectious agent, prior to addition of lysis buffer and substrate. These additional washing steps aid in the removal of excess parental phage and/or luciferase or other reporter protein contaminating the phage preparation. Accordingly, in some embodiments, the method of the detecting antibiotic resistance may comprise washing the captured and infected microorganisms, after adding the phage but before incubating.

In many embodiments, multi-well plates are used to conduct the assays. The choice of plates (or any other container in which detecting may be performed) may affect the detecting step. For example, some plates may include a colored or white background, which may affect the detection of light emissions. Generally speaking, white plates have higher sensitivity but also yield a higher background signal. Other colors of plates may generate lower background signal but also have a slightly lower sensitivity. Additionally, one reason for background signal is the leakage of light from one well to another, adjacent well. There are some plates that have white wells but the rest of the plate is black. This allows for a high signal inside the well but prevents well-to-well light leakage and thus may decrease background. Thus the choice of plate or other assay vessel may influence the sensitivity and background signal for the assay.

Thus, some embodiments of the present invention solve a need by using infectious agent-based methods for amplifying a detectable signal, thereby indicating whether a microorganism is resistant to an antibiotic. The invention allows a user to detect antibiotic resistance of a microorganism that is present in a sample although the sample has not been enriched or cultured. In certain embodiments as little as a single bacterium is detected. This principle allows amplification of indicator signal from one or a few cells based on specific recognition of microorganism surface receptors. For example, by exposing even a single cell of a microorganism to a plurality of phage, thereafter allowing amplification of the phage and high-level expression of an encoded indicator gene product during replication, the indicator signal is amplified such that the single microorganism is detectable. The methods of the present invention provide high detection sensitivity and specificity rapidly and without the need for traditional biological enrichment (e.g., culturing for enrichment). In some embodiments detection is possible within 1-2 replication cycles of the phage or virus, which goes against conventional wisdom, as it does not take advantage of the phage's natural ability to amplify itself and the signal of the indicator moiety.

In additional embodiments, the invention comprises systems (e.g., computer systems, automated systems or kits) comprising components for performing the methods disclosed herein, and/or using the modified infectious agents described herein.

Systems and Kits of the Invention

In some embodiments, the invention comprises systems (e.g., automated systems or kits) comprising components for performing the methods disclosed herein. These systems and kits of the invention include various components. As used herein, the term "component" is broadly defined and includes any suitable apparatus or collections of apparatuses suitable for carrying out the recited method. The components need not be integrally connected or situated with respect to each other in any particular way. The invention includes any suitable arrangements of the components with respect to each other. For example, the components need not be in the same room. But in some embodiments, the components are connected to each other in an integral unit. In some embodiments, the same components may perform multiple functions.

Some embodiments described herein are particularly suitable for automation or kits, given the minimal amount of reagents and materials required to perform the methods. In certain embodiments, each of the components of a kit may comprise a self-contained unit that is deliverable from a first site to a second site.

In some embodiments, the invention comprises systems or kits for rapid detection of resistance to an antibiotic of a microorganism of interest in a sample. The systems or kits may in certain embodiments comprise a component for incubating the sample with the antibiotic, a component for incubating the sample with an infectious agent specific for the microorganism of interest, wherein the infectious agent comprises an indicator moiety, and a component for detecting the indicator moiety. In some embodiments of both the systems and the kits of the invention, the infectious agent is a recombinant phage that infects the microorganism of interest, and the recombinant phage comprises an indicator gene inserted into a late gene region of the phage as the indicator moiety such that expression of the indicator gene during phage replication following infection of host bacteria results in a soluble indicator protein product. Some systems further comprise a component for capturing the microorganism of interest on a solid support and/or a component for lysing the microorganism after incubation with the infectious agent to release progeny infectious agents and soluble indicator proteins present in the microorganism.

In certain embodiments, the systems and/or kits may further comprise a component for washing the captured microorganism sample. Additionally or alternatively, the systems and/or kits may further comprise a component for determining the amount of the indicator moiety, wherein the amount of the indicator moiety detected corresponds to the amount of microorganisms in the sample that have been treated by antibiotic, which corresponds to the antibiotic resistance in the sample. For example, in certain embodiments, the system or kit may comprise a luminometer or other device for measuring a luciferase enzyme activity. In some embodiments, the same component may be used for steps of capturing and/or incubating and/or washing. Some embodiments additionally comprise a component for determining the number of microorganisms of interest in the sample, wherein the amount of indicator moiety detected corresponds to the number of microorganisms in the sample.

In some systems and/or kits, the same component may be used for multiple steps. In some systems and/or kits, the steps are automated or controlled by the user via computer input and/or wherein a liquid-handling robot performs at least one step. In some embodiments, the systems and/or kit may comprise a component for isolated the microorganism of interest from the other components in the sample before contacting with the antibiotic.

Also provided herein is a system and/or kit for determining the effective dose of an antibiotic for killing or inhibiting a microorganism. In some embodiments, the kit comprises an infectious agent, and reagents, e.g., for preparing a one or more antibiotic solutions having different concentrations such that the different concentrations of the solution define a range. In some cases, two or more antibiotic solutions are tested and the concentration ratio of the least concentrated antibiotic solution to the most concentrated antibiotic solution in the one or more antibiotic solutions ranges from 1:2 to 1:50, e.g., from 1:5 to 1:30, or from 1:10 to 1:20. In some cases, the lowest concentration of the one or more antibiotic solution is at least 1 µg/mL, e.g., at least 2 µg/mL, at least 5 µg/mL, at least 10 µg/mL, at least 20 µg/mL, at least 40 µg/mL, at least 80 µg/mL, or at least 100 µg/mL. The kit may also comprise components for incubating each of the one or more antibiotic solutions with a microorganism of interest in a sample.

In other embodiments, the invention may comprise a kit for rapid detection of the resistance to an antibiotic of a microorganism of interest in a sample, the kit comprising the antibiotic, and an infectious agent specific for the microorganism of interest, wherein the infectious agent comprises an indicator moiety. Optionally, the kit may comprise a filter and/or a capture antibody for capturing the microorganism of interest. Optionally, the kit comprises buffers for washing the captured microorganism sample to remove unbound infectious agent. Optionally, the kit comprises a substrate that can react with the indicator moiety to produce a detectable signal. Such kits can include various embodiments and sub-embodiments analogous to those described above for methods of rapid detection of microorganisms. In an embodiment, the microorganism is a bacterium and the infectious agent is a phage.

The kits may comprise a variety of components for detection of progeny infectious agents. For example, in an embodiment, the progeny infectious agent (e.g., phage) may comprise an indicator moiety. In an embodiment, the indicator moiety in the progeny infectious agent (e.g., phage) may be a detectable moiety that is expressed during replication, such as a soluble luciferase protein.

Computer Systems and Computer Readable Media

The system, as described in the present technique or any of its components, may be embodied in the form of a computer system. Typical examples of a computer system include a general-purpose computer, a programmed microprocessor, a microcontroller, a peripheral integrated circuit element, and other devices or arrangements of devices that are capable of implementing the steps that constitute the method of the present technique. Exemplar computer systems and computer readable media that can be used for the system, methods of the present invention are described in US Patent Publication No. 2015/0218616, and the relevant disclosure is hereby incorporated by reference in its entirety.

While the present invention has been disclosed with references to certain embodiments, numerous modifications, alterations and changes to the described embodiments are possible without departing from the scope and spirit of the present invention, as defined in the appended claims. Accordingly, it is intended that the present invention not be limited to the described embodiments, but that it have the full scope defined by the language of the following claims, and equivalents thereof.

EXAMPLES

The following examples are to illustrate but not limit the invention.

Example 1. Determining Antibiotic Resistance Using Bacteriophage

About $1\times10^6$ cells/well of E. coli O157:H7 were transferred to a 96-well plate at 100 µL per well. 10 µL of ampicillin or vancomycin solution were added to the wells to reach a final concentration of 10 µg/mL, 25 µg/mL, 50 µg/mL, 100 µg/mL, or 200 µg/mL of ampicillin or vancomycin. Ampicillin targets both Gram-negative and Gram-positive bacteria and vancomycin targets only Gram-positive bacteria. Buffer solutions without either antibiotic were also prepared and added to cells to serve as controls. Samples were incubated with either antibiotic or the control at 37° C. for 30 minutes and then incubated with $1\times10^6$ phage particles/mL of CBA120NanoLuc phage at 37° C. for 120 min. The CBA120NanoLuc phage was derived from the CBA120 phage and can specifically infect E. coli O157:H7 and produce luciferase when replicating in host cells. 10 µL of lysis buffer was added to each of the wells, which was followed by the addition of 50 µL of prepared luciferase reagent. Luminescence from the reactions were read on a GLOMAX® Navigator and relative luminescence units (RLU) for each reaction were plotted and analyzed. The signal provided by the soluble luciferase produced upon infection of the bacteria is shown on the Y-axis as RLU.

The results, shown in FIG. 1, indicate that treating cells with ampicillin at concentrations of 10 µg/mL, 25 µg/mL, or 50 µg/mL caused a signal reduction of about 100-fold, 1400-fold, or 2200-fold, respectively, as compared to controls. On the other hand, signals increased upon exposure to vancomycin at 10 µg/mL, 25 µg/mL, 50 µg/mL, or 100 µg/mL. This result shows that the cells were resistant to vancomycin but sensitive to ampicillin. The high RLU values of the reactions suggest the assay is highly sensitive and that antibiotic sensitivity or resistance can be measured for samples having even lower cell concentrations without any enrichment incubation.

Example 2. Determining Antibiotic Resistance Using Bacteriophage

Bacterial strains were serially diluted to approximately $1\times10^3$ CFU/mL and transferred to a 96-well plate at 135 µL per well. 15 μL of oxacillin or cefoxitin were added to the wells to reach a final concentration of 1.0 μg/mL or 2.0 μg/mL of oxicillin or 2.0 μg/mL, 4.0 μg/mL, 8.0 μg/mL, or 10.0 μg/mL of cefoxitin. The plate was then sealed and incubated at 37° C. for 2 hours. 10 μL of recombinant phage ($1.6 \times 10^8$ pfu/mL) was added to each well. The plate was then re-sealed and incubated at 37° C. for 2 hours. A master mix was made containing 15 μL 5× lysis buffer, 50 μL luciferase assay buffer, and 1 μL luciferase substrate per well. 65 μL of master mix was added to each well. Luminescence from the reactions was read on a GLOMAX® Navigator and relative luminal units (RLU) for each reaction were analyzed. RLU values three times greater than an established background RLU level for LB (>750 RLU) were considered positive. The results, shown in Table 1, indicate that the recombinant phage are capable of detecting the tested bacterial strains. Each of the tested bacterial strains not treated with antibiotic (0 ug/mL) had positive RLU values indicating that the bacterium of interest was present in the sample.

Additionally, incubation with oxacillin resulted in no detection for several MRSA and MSSA strains. Incubation with cefoxitin (2 ug/mL) resulted in selective loss of MSSA detection, indicating that these MSSA strains are susceptible to cefoxitin. Positive results are in bold.

Example 3. Optimization of Cefoxitin Concentration for Sensitivity

Bacterial strains were serially diluted to approximately $1 \times 10^3$ CFU/mL and transferred to a 96-well plate at 135 μL per well. 15 μL of cefoxitin was added to the wells to reach a final concentration of 1.4 μg/mL, 1.6 μg/mL, 1.8 μg/mL or 2.0 μg/mL. The plate was then sealed and incubated at 37° C. for 2 hours. 10 μL of recombinant phage ($1.6 \times 10^8$ pfu/mL) was added to each well. The plate was then re-sealed and incubated at 37° C. for an additional 2 hours. A master mix was made containing 15 μL 5× lysis buffer, 50 μL luciferase assay buffer, and 1 μL luciferase substrate per well. 65 μL of master mix was added to each well. Luminescence from the reactions were read on a GLOMAX® Navigator and relative luminal units (RLU) for each reaction were plotted and analyzed. RLU values three times greater than an established background RLU level for LB (>750 RLU) were considered positive. The results, shown in Table 2, indicate that the recombinant phage are capable of detecting these bacterial strains. Each of the tested bacterial strains not treated with antibiotic (0 ug/mL) had positive RLU values indicating that the bacterium of interest was present in the sample allowing for infection by the recombinant phage and detection of a luciferase product. A cefoxitin concentration of 1.8 ug/mL was found to selectively inhibit a positive signal from most MSSA strains, while most of the tested MRSA strains produced a positive signal. Positive results are in bold.

TABLE 1

Comparison of Cefoxitin and Oxacillin for MRSA Detection

| Strain | Source | Classification | Detected CFU | Oxacillin (RLU) | | | Cefoxitin (RLU) | | | |
|---|---|---|---|---|---|---|---|---|---|---|
| | | | | 0 ug/mL | 1 ug/mL | 2 ug/mL | 2 ug/mL | 4 ug/mL | 8 ug/mL | 10 ug/mL |
| BAA-1720 | ATCC | MRSA | 201 | 22630 | 23810 | 22560 | 14910 | 11250 | 7123 | 6431 |
| AR0463 | From CDC Borderline Oxacillin Panel | MRSA | 419 | 21370 | 426 | 353 | 1125 | 349 | 287 | 246 |
| AR0465 | From CDC Borderline Oxacillin Panel | MRSA | 111 | 8831 | 4944 | 4965 | 7815 | 5254 | 4619 | 2869 |
| AR0472 | From CDC Borderline Oxacillin Panel | MRSA | 190 | 29440 | 348 | 281 | 3538 | 229 | 239 | 220 |
| AR0476 | From CDC Borderline Oxacillin Panel | MRSA | 194 | 66450 | 553 | 212 | 1202 | 213 | 204 | 248 |
| AR0481 | From CDC Borderline Oxacillin Panel | MRSA | 43 | 3335 | 467 | 268 | 3499 | 983 | 222 | 250 |
| 12600 | ATCC | MSSA | 389 | 48030 | 1459 | 697 | 797 | 475 | 332 | 277 |
| AR0484 | From CDC Borderline Oxacillin Panel | MSSA | 153 | 10200 | 268 | 219 | 227 | 195 | 197 | 204 |
| AR0488 | From CDC Borderline Oxacillin Panel | MSSA | 285 | 21600 | 228 | 198 | 254 | 220 | 213 | 229 |
| AR0491 | From CDC Borderline Oxacillin Panel | MSSA | 300 | 21820 | 245 | 221 | 207 | 234 | 187 | 191 |
| LB | MP Cat NO. 3002-132 | Control | 0 | 222 | 243 | 221 | 214 | 242 | 206 | 206 |

TABLE 2

Optimization of Cefoxitin concentration for sensitivity

| Strain | Source | Classification | Detected CFU | Cefoxitin Concentration | | | | |
|---|---|---|---|---|---|---|---|---|
| | | | | 0 ug/mL | 1.4 ug/mL | 1.6 ug/mL | 1.8 ug/mL | 2 ug/mL |
| AR0461 | CDC Borderline Oxacillin Panel | MRSA | 140 | 11840 | 9488 | 11490 | 9510 | 11130 |
| AR0463 | CDC Borderline Oxacillin Panel | MRSA | 389 | 20230 | 6364 | 4531 | 2854 | 1501 |
| AR0465 | CDC Borderline Oxacillin Panel | MRSA | 99 | 6765 | 6380 | 6276 | 4614 | 4856 |
| AR0467 | CDC Borderline Oxacillin Panel | MRSA | 198 | 7002 | 7382 | 6887 | 5736 | 6615 |
| AR0468 | CDC Borderline Oxacillin Panel | MRSA | 205 | 6786 | 7270 | 7067 | 7461 | 8849 |
| AR0469 | CDC Borderline Oxacillin Panel | MRSA | 473 | 19030 | 11090 | 14270 | 13490 | 15040 |
| AR0470 | CDC Borderline Oxacillin Panel | MRSA | 314 | 2409 | 2490 | 2481 | 2046 | 1524 |
| AR0472 | CDC Borderline Oxacillin Panel | MRSA | 79 | 12720 | 15170 | 12160 | 11480 | 9511 |
| AR0473 | CDC Borderline Oxacillin Panel | MRSA | 583 | 85510 | 72470 | 57470 | 41950 | 34010 |
| AR0475 | CDC Borderline Oxacillin Panel | MRSA | 409 | 50360 | 71710 | 80640 | 73340 | 84240 |
| AR0476 | CDC Borderline Oxacillin Panel | MRSA | 198 | 90600 | 53760 | 38590 | 27110 | 18720 |
| AR0477 | CDC Borderline Oxacillin Panel | MRSA | 178 | 58230 | 38090 | 32240 | 24570 | 16550 |
| AR0478 | CDC Borderline Oxacillin Panel | MRSA | 205 | 105400 | 52240 | 50530 | 31980 | 21410 |
| AR0479 | CDC Borderline Oxacillin Panel | MRSA | 186 | 76160 | 49750 | 35370 | 26790 | 35620 |
| AR0480 | CDC Borderline Oxacillin Panel | MRSA | 205 | 74630 | 42740 | 50910 | 41630 | 32020 |
| AR0481 | CDC Borderline Oxacillin Panel | MRSA | 149 | 84200 | 64170 | 71090 | 51050 | 68790 |
| AR0482 | CDC Borderline Oxacillin Panel | MRSA | 319 | 6049 | 5278 | 4707 | 3181 | 3401 |
| AR0483 | CDC Borderline Oxacillin Panel | MRSA | 105 | 37160 | 31500 | 22700 | 28940 | 21470 |
| BAA-2094 | ATCC | MRSA | 139 | 17110 | 5593 | 3511 | 1839 | 1620 |
| BAA-2313 | ATCC | MRSA | 192 | 36990 | 8601 | 5620 | 3239 | 2385 |
| BAA-42 | ATCC | MRSA | 169 | 2956 | 1827 | 1520 | 1392 | 643 |
| 12600 | ATCC | MSSA | 401 | 18730 | 2489 | 1596 | 974 | 750 |
| AR0484 | CDC Borderline Oxacillin Panel | MSSA | 107 | 7968 | 174 | 176 | 187 | 181 |
| AR0485 | CDC Borderline Oxacillin Panel | MSSA | 248 | 17100 | 1328 | 812 | 655 | 404 |
| AR0486 | CDC Borderline Oxacillin Panel | MSSA | 163 | 24720 | 4238 | 1743 | 1099 | 794 |
| AR0487 | CDC Borderline Oxacillin Panel | MSSA | 198 | 7182 | 336 | 227 | 204 | 165 |
| AR0488 | CDC Borderline Oxacillin Panel | MSSA | 360 | 57240 | 2274 | 1149 | 402 | 256 |
| AR0489 | CDC Borderline Oxacillin Panel | MSSA | 186 | 15340 | 6208 | 3172 | 2029 | 870 |
| AR0490 | CDC Borderline Oxacillin Panel | MSSA | 109 | 11900 | 1277 | 598 | 423 | 258 |
| AR0491 | CDC Borderline Oxacillin Panel | MSSA | 239 | 10750 | 1438 | 676 | 518 | 338 |
| AR0492 | CDC Borderline Oxacillin Panel | MSSA | 130 | 41150 | 1883 | 839 | 556 | 246 |
| BAA-1721 | ATCC | MSSA | 166 | 41300 | 2753 | 1087 | 441 | 258 |

Example 4. Determining Antibiotic Resistance Using Bacteriophage

Bacterial strains were serially diluted and Copan e-Swabs™ were inoculated with 100 µL of LB with approximately the target number of cells of 1000 CFU, 500 CFU, 250 CFU, 125 CFU, 63 CFU, 31 CFU, 16 CFU, or 8 CFU. Swabs were then eluted in 1 mL modified Amies solution (included with commercially available Copan e-Swabs™). 135 µL of this solution was added to each well of a 96-well plate. 15 µL of cefoxitin was added to the wells to reach a final concentration of 1.8 µg/mL, 3.6 µg/mL, or 5.4 µg/mL. The plate was then sealed and incubated at 37° C. for 2 hours. 10 µL of recombinant phage ($1.6 \times 10^8$ pfu/mL) was added to each well. The plate was then re-sealed and incubated at 37° C. for an additional 2 hours. A master mix was made containing 15 µL 5× lysis buffer, 50 µL luciferase assay buffer, and 1 µL luciferase substrate per well. 65 µL of master mix was added to each well. Luminescence from the reactions was read on a GLOMAX® Navigator and relative luminal units (RLU) for each reaction were plotted and analyzed. RLU values three times greater than an established background RLU level for modified Amies solution (>1500 RLU) were considered positive. The results, shown in Table 3, indicate that a positive MRSA determination was made with 17 CFU in a well, originating from approximately 125 CFU on a swab when incubated with the previously established cut-off of 1.8 µg/mL. Positive results are in bold.

TABLE 3

MRSA Detection is Compatible with Copan e-Swabs ™

| | | | | | Cefoxitin (RLU) | | | |
| --- | --- | --- | --- | --- | --- | --- | --- | --- |
| Strain | Source | Classification | Target Swab CFU | Detected CFU | 0 ug/mL | 1.8 ug/mL | 3.6 ug/mL | 5.4 ug/mL |
| BAA-1720 | ATCC | MRSA | 1000 | 136 | 34170 | 23820 | 17540 | 18400 |
| BAA-1720 | ATCC | MRSA | 500 | 72 | 14730 | 11590 | 7112 | 7648 |
| BAA-1720 | ATCC | MRSA | 250 | 41 | 6729 | 3766 | 4022 | 3374 |
| BAA-1720 | ATCC | MRSA | 125 | 17 | 4729 | 2512 | 1337 | 2501 |
| BAA-1720 | ATCC | MRSA | 63 | 9 | 3379 | 1280 | 1568 | 1286 |
| BAA-1720 | ATCC | MRSA | 31 | 1 | 1515 | 880 | 558 | 1405 |
| BAA-1720 | ATCC | MRSA | 16 | 1 | 814 | 1179 | 470 | 551 |
| BAA-1720 | ATCC | MRSA | 8 | 1 | 704 | 559 | 429 | 336 |
| Amies | Copan e-Swab ™ | Control | | 0 | 425 | | | |

Example 5. Determining Antibiotic Resistance Using Bacteriophage

Bacterial strains were serially diluted and BD BBL CultureSwabs™ were inoculated with 50 ul of LB with approximately the target number of cells of 1000 CFU, 500 CFU, 250 CFU, 125 CFU, 63 CFU, 31 CFU, 16 CFU, or 8 CFU. Swabs were eluted with 1 mL modified Amies solution (included with commercially available Copan e-Swabs™). 135 µL of the eluted solution was added to each well. 15 µL of cefoxitin was added to the wells to reach a final concentration of 1.8 µg/mL, 3.6 µg/mL, or 5.4 µg/mL. The plate was then sealed and incubated at 37° C. for 2 hours. 10 µL of recombinant phage (1.6×10⁸ pfu/mL) was added to each well. The plate was then re-sealed and incubated at 37° C. for an additional 2 hours. A master mix was made containing 15 µL 5× lysis buffer, 50 µL luciferase assay buffer, and 1 µL luciferase substrate per well. 65 µL of master mix was added to each well. Luminescence from the reactions were read on a GLOMAX® Navigator and relative luminal units (RLU) for each reaction were plotted and analyzed. RLU values three times greater than an established background RLU level for modified Amies solution (>1500 RLU) were considered positive. The results, shown in Table 4, indicate that a positive MRSA determination was made with 23 CFU in a well, originating from approximately 125 CFU on a swab when incubated with the previously established cut-off of 1.8 µg/mL. Positive results are highlighted in grey.

TABLE 4

MRSA Detection is Compatible with BD BBL CultureSwabs ™

| | | | | | Cefoxitin (RLU) | | | |
| --- | --- | --- | --- | --- | --- | --- | --- | --- |
| Strain | Source | Classification | Target Swab CFU | Detected CFU | 0 ug/mL | 1.8 ug/mL | 3.6 ug/mL | 5.4 ug/mL |
| BAA-1720 | ATCC | MRSA | 1000 | 76 | 15420 | 13210 | 7193 | 6922 |
| BAA-1720 | ATCC | MRSA | 500 | 31 | 9708 | 7571 | 7693 | 5263 |
| BAA-1720 | ATCC | MRSA | 250 | 28 | 6332 | 6254 | 3843 | 3381 |
| BAA-1720 | ATCC | MRSA | 125 | 23 | 6937 | 3630 | 4720 | 4597 |
| BAA-1720 | ATCC | MRSA | 63 | 5 | 1547 | 900 | 1068 | 948 |
| BAA-1720 | ATCC | MRSA | 31 | 4 | 2603 | 3572 | 1469 | 1438 |
| BAA-1720 | ATCC | MRSA | 16 | 1 | 550 | 1711 | 1623 | 1172 |
| BAA-1720 | ATCC | MRSA | 8 | 3 | 479 | 615 | 513 | 789 |
| Amies | Copan e-Swab ™ | Control | | 0 | 530 | | | |

Example 6. Effect of Duration with Antibiotic and Phage Exposure on MSSA Signal

Bacterial strains were serially diluted and transferred to a 96-well plate at 135 µL per well. 15 µL of cefoxitin was added to the wells to reach a final concentration of 1.8 µg/mL, 3.6 µg/mL, or 5.4 µg/mL. The plate was then sealed and incubated at 37° C. for 2 hours or 3 hours. 10 µL of recombinant phage (1.6×10⁸ pfu/mL) was added to each well. The plate was then re-sealed and incubated at 37° C. for an additional 1 or 2 hours. A master mix was made containing 15 µL 5× lysis buffer, 50 µL luciferase assay buffer, and 1 µL luciferase substrate per well. 65 µL of master mix was added to each well. Luminescence from the reactions was read on a GLOMAX® Navigator and relative luminal units (RLU) for each reaction were plotted and analyzed. RLU values three times greater than an established background RLU level for LB (>750 RLU) were considered positive. The results, shown in Table 5, indicate that the number of MSSA strains producing false-positives at the previously established cut-off of 1.8 µg/mL cefoxitin were reduced with a 3-hour antibiotic/1-hour phage protocol when compared to a 2-hour antibiotic/2-hour phage protocol. A false positive occurred at 541 CFU with the 2-hour antibiotic/2-hour phage protocol. Whereas, the 3-hour antibiotic/1-hour phage protocol produced false positives at 4331 CFU. Positive results are in bold. In Table 5, CFU values (541 CFU and 305 CFU) were experimentally validated by direct plating.

TABLE 5

Effect of Duration with antibiotic and phage exposure on MSSA Signal

| | | | | Cefoxitin (RLU) - 2 Hour Antibiotic + 2 Hour Phage | | | | Cefoxitin (RLU) - 3 Hour Antibiotic + 1 Hour Phage | | | |
|---|---|---|---|---|---|---|---|---|---|---|---|
| Strain | Source | Classification | Detected CFU | 0 ug/mL | 1.8 ug/mL | 3.6 ug/mL | 5.4 ug/mL | 0 ug/mL | 1.8 ug/mL | 3.6 ug/mL | 5.4 ug/mL |
| 12600 | ATCC | MSSA | 17323 | 2619000 | 22890 | 2071 | 1493 | 1022000 | 2695 | 255 | 246 |
| 12600 | ATCC | MSSA | 8662 | 1145000 | 11570 | 1224 | 979 | 489900 | 1563 | 247 | 224 |
| 12600 | ATCC | MSSA | 4331 | 502100 | 5703 | 563 | 487 | 273400 | 933 | 196 | 194 |
| 12600 | ATCC | MSSA | 2165 | 215500 | 3046 | 424 | 331 | 142500 | 604 | 218 | 202 |
| 12600 | ATCC | MSSA | 1083 | 109700 | 1718 | 395 | 277 | 70400 | 415 | 201 | 208 |
| 12600 | ATCC | MSSA | 541 | 52310 | 1065 | 224 | 217 | 34480 | 258 | 215 | 171 |
| 12600 | ATCC | MSSA | 305 | 25880 | 600 | 225 | 244 | 18420 | 267 | 198 | 184 |
| 12600 | ATCC | MSSA | 0 | 149 | 176 | 155 | 154 | 176 | 194 | 215 | 181 |

Example 7. Detection of MRSA in Co-Culture with MSSA

Bacterial strains were serially diluted and transferred to a 96-well plate at 135 µL per well. 15 µL of cefoxitin was added to the wells to reach a final concentration of 1.8 µg/mL. The plate was then sealed and incubated at 37° C. for 2 hours or 3 hours. 10 µL of recombinant phage (1.6×10$^8$ pfu/mL) was added to each well. The plate was then re-sealed and incubated at 37° C. for an additional 1 or 2 hours. A master mix was made containing 15 µL 5× lysis buffer, 50 µL luciferase assay buffer, and 1 µL luciferase substrate per well. 65 µL of master mix was added to each well. Luminescence from the reactions was read on a GLOMAX® Navigator and relative luminal units (RLU) for each reaction were plotted and analyzed. RLU values three times greater than an established background RLU level for LB (>750 RLU) were considered positive. The results, shown in Table 6, indicate that samples with MRSA (38 CFU) can be distinguished from samples containing MSSA (up to 5088 CFU) using a 3-hour antibiotic/1-hour phage incubation protocol. Positive results are in bold. In Table 6, CFU values (318 CFU and 156 CFU) were experimentally validated by direct plating.

TABLE 6

Detection of MRSA in Co-culture with MSSA

| | | 2 HR AB + 2 HR Phage | | 3 HR AB + 1 HR Phage | |
|---|---|---|---|---|---|
| 12600 - MSSA Detected CFU | BAA-1720 - MRSA Detected CFU | 0 ug/mL | 1.8 ug/mL | 0 ug/mL | 1.8 ug/mL |
| 10176 | 0 | 1450000 | 16340 | 841000 | 1098 |
| 5088 | 0 | 627000 | 8583 | 661200 | 901 |
| 2544 | 0 | 321700 | 4715 | 290800 | 621 |
| 1272 | 0 | 141300 | 1685 | 110000 | 321 |
| 636 | 0 | 74870 | 956 | 72820 | 275 |
| 318 | 0 | 34290 | 608 | 31840 | 231 |
| 156 | 0 | 19320 | 423 | 13230 | 196 |
| 0 | 0 | 180 | 182 | 188 | 198 |
| 10176 | 38 | 1646000 | 13260 | 744000 | 5347 |
| 5088 | 38 | 748700 | 11400 | 334900 | 3548 |
| 2544 | 38 | 304100 | 10730 | 167300 | 3749 |
| 1272 | 38 | 147100 | 6263 | 93840 | 4930 |
| 636 | 38 | 78480 | 7217 | 42270 | 3946 |
| 318 | 38 | 42700 | 7143 | 26380 | 4567 |
| 156 | 38 | 25200 | 5084 | 13680 | 3976 |
| 0 | 38 | 5995 | 4218 | 5338 | 3136 |

We claim:

1. A method of detecting antibiotic-resistant bacteria in a sample comprising:
   (a) contacting the sample with an antibiotic,
   (b) contacting the sample with a recombinant bacteriophage specific to the bacteria, wherein the recombinant bacteriophage comprises a genetic construct inserted into a late gene region of the bacteriophage genome, the genetic construct comprising:
      (i) an indicator gene, wherein the indicator gene is not contiguous with a gene encoding a structural bacteriophage protein and does not yield a fusion protein; and
      (ii) a promoter controlling transcription of the indicator gene, wherein the promoter is a bacteriophage late promoter,
   and wherein expression of the indicator gene results in an indicator protein product, and wherein the indicator protein product is a luciferase;

(c) detecting a signal produced by the indicator protein product,
   wherein detection of the signal is used to determine the presence of antibiotic-resistant bacteria in the sample.

2. The method of claim 1, wherein the sample is contacted with the antibiotic for a period of time before contacting the infectious agent.

3. The method of claim 1, wherein the method further comprises lysing the bacteria in the sample before detecting the indicator protein.

4. The method of claim 1, wherein contacting the bacteria with the recombinant bacteriophage lasts less than 4 hours.

5. The method of claim 1, wherein the sample is incubated with the antibiotic for a period of from 5 min to 24 hours prior to contact with the recombinant bacteriophage.

6. The method of claim 1, wherein the sample is incubated with the antibiotic for a period of from 5 min to 3 hours prior to contact with the recombinant bacteriophage.

7. The method of claim 1, wherein the antibiotic is selected from the group consisting of aminoglycosides, carbacephems, carbapenems, cephalosporins, glycopeptides, macrolides, monobactams, penicillin, beta-lactam antibiotic, quinolones, bacitracin, sulfonamides, tetracyclines, streptogramines, chloramphenicol, clindamycin, and lincosamide, cephamycins, lincomycins, daptomycin, oxazolidinone, and glycopeptide antibiotic.

8. The method of claim 1, wherein the recombinant bacteriophage comprises an indicator gene inserted into a late gene region of the bacteriophage genome.

9. The method of claim 1, wherein the indicator gene is adjacent to a major capsid gene.

10. The method of claim 1, wherein the recombinant bacteriophage is derived from phage K, Twort, Twort-like, NCTC 9857, Vil, Vil-like, T7, T4, or T4-like.

11. The method of claim 1, wherein the bacterium is *Staphylococcus aureus* and the recombinant bacteriophage is highly specific for *Staphylococcus aureus*.

12. The method of claim 1, wherein the bacterium is comprised in an uncultured sample.

13. The method of claim 1, wherein the bacterium is comprised in a sample, wherein the sample is a clinical, food, environmental, or water sample.

14. The method of claim 1, wherein the signal produced by the sample is compared to an experimentally determined value, wherein the experimentally determined value is the signal produced by a control sample.

15. The method of claim 14, wherein the experimentally determined value is a background threshold value calculated from an average background signal plus standard deviation of 1-3 times the average background signal, or greater.

16. The method of claim 15, wherein detection of a signal produced by the sample greater than the background threshold value indicates the presence of one or more antibiotic-resistant bacteria in the sample.

17. A method of determining effective dose of an antibiotic in killing bacteria comprising:
   (a) incubating each of one or more of antibiotic solutions separately with one or more samples comprising the bacteria, wherein the concentrations of the one or more of antibiotic solutions are different and define a range;
   (b) incubating the bacteria in the one or more samples with a recombinant bacteriophage specific to the bacteria, wherein the recombinant bacteriophage comprises a genetic construct inserted into a late gene region of the bacteriophage genome, the genetic construct comprising:
      (i) an indicator gene, wherein the indicator gene is not contiguous with a gene encoding a structural bacteriophage protein and does not yield a fusion protein; and
      (ii) a promoter controlling transcription of the indicator gene, wherein the promoter is a bacteriophage late promoter,
   and wherein expression of the indicator gene results in an indicator protein product, and wherein the indicator protein product is a luciferase; and
   (c) detecting the indicator protein product, wherein detection of the indicator protein product in the one or more samples indicates the concentrations of antibiotic solutions used to treat the one or more samples are not effective, and the lack of detection of the indicator protein indicates the antibiotic is effective, thereby determining the effective dose of the antibiotic.

18. The method of claim 17, wherein the one or more antibiotic solutions are two or more antibiotic solutions, and wherein the concentration ratio of the least concentrated solution and the most concentrated solution in the plurality of antibiotic solutions ranges from 1:2 to 1:50.

19. A kit for detecting antibiotic-resistant bacteria in a sample, wherein the kit comprises:
   (a) a recombinant bacteriophage specific to the bacteria, wherein the recombinant bacteriophage comprises a genetic construct inserted into a late gene region of the bacteriophage genome, the genetic construct comprising:
      (i) an indicator gene, wherein the indicator gene is not contiguous with a gene encoding a structural bacteriophage protein and does not yield a fusion protein; and
      (ii) a promoter controlling transcription of the indicator gene, wherein the promoter is a bacteriophage late promoter, and wherein expression of the indicator gene results in an indicator protein product, and wherein the indicator protein product is a luciferase; and
   (b) an antibiotic.

20. The kit of claim 19, further comprising a substrate for detecting an indicator protein product.

21. A system for detecting antibiotic resistance of bacteria in a sample, comprising
   a recombinant bacteriophage specific to the bacteria, wherein the recombinant bacteriophage comprises a genetic construct inserted into a late gene region of the bacteriophage genome, the genetic construct comprising:
      (i) an indicator gene, wherein the indicator gene is not contiguous with a gene encoding a structural bacteriophage protein and does not yield a fusion protein; and
      (ii) a promoter controlling transcription of the indicator gene, wherein the promoter is a bacteriophage late promoter,
   and wherein expression of the indicator gene results in an indicator protein product, and wherein the indicator protein product is a luciferase;
   a component for contacting the sample with the antibiotic,
   a component for contacting the sample with the recombinant bacteriophage specific to the bacteria; and
   a component for detecting the protein product in the sample that has contacted the recombinant bacteriophage, wherein positive detection of the indicator protein product indicates the bacteria is resistant to the antibiotic.

\* \* \* \* \*